United States Patent
Dejima

(10) Patent No.: US 10,264,950 B2
(45) Date of Patent: *Apr. 23, 2019

(54) ENDOSCOPIC SURGERY DEVICE

(71) Applicant: FUJIFILM Corporation, Tokyo (JP)

(72) Inventor: Takumi Dejima, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/868,398

(22) Filed: Sep. 29, 2015

(65) Prior Publication Data

US 2016/0015255 A1    Jan. 21, 2016

Related U.S. Application Data

(63) Continuation of application No. PCT/JP2014/058778, filed on Mar. 27, 2014.

(30) Foreign Application Priority Data

Mar. 29, 2013  (JP) ................. 2013-074014

(51) Int. Cl.
*A61B 1/00* (2006.01)
*A61B 1/313* (2006.01)
(Continued)

(52) U.S. Cl.
CPC ...... *A61B 1/00087* (2013.01); *A61B 1/00131* (2013.01); *A61B 1/00133* (2013.01);
(Continued)

(58) Field of Classification Search
CPC ............ A61B 1/00131; A61B 1/00133; A61B 1/00135; A61B 1/0014; A61B 1/00142;
(Continued)

(56) References Cited

U.S. PATENT DOCUMENTS 4,538,594 A   9/1985  Boebel et al.
4,610,242 A   9/1986  Santangelo et al.
(Continued)

FOREIGN PATENT DOCUMENTS

JP    08-140988    6/1996
JP    08-164148    6/1996
(Continued)

OTHER PUBLICATIONS

"Written Opinion of the International Searching Authority of PCT/JP2014/058778", dated May 13, 2014, with English translation thereof, pp. 1-9.

(Continued)

*Primary Examiner* — Ryan N Henderson
(74) *Attorney, Agent, or Firm* — JCIPRNET

(57) ABSTRACT

An insertion part of an endoscope and an insertion part of a treatment tool, which are inserted in an outer tube, can be synchronously moved in the axial direction, and, even when the insertion part of the treatment tool is slightly moved in the axial direction, an excellent endoscopic image without shake is obtained. When a treatment tool of an endoscopic surgery device moves by a displacement amount over an allowance amount, an endoscope moves in interlock with the movement of the treatment tool. Moreover, the treatment tool 50 moves in the axial direction with the allowance amount t with respect to the endoscope 10. Therefore, when the treatment tool is moved by a displacement amount of allowance amount or less, the endoscope does not move. By providing such allowance amount, slight movement of the treatment tool is not transmitted to the endoscope.

18 Claims, 25 Drawing Sheets

(51) Int. Cl.
*A61B 17/34* (2006.01)
*A61B 1/06* (2006.01)
*A61B 90/00* (2016.01)

(52) U.S. Cl.
CPC ...... *A61B 1/00135* (2013.01); *A61B 1/00154* (2013.01); *A61B 1/0676* (2013.01); *A61B 1/313* (2013.01); *A61B 1/3132* (2013.01); *A61B 17/3421* (2013.01); *A61B 17/3423* (2013.01); *A61B 17/3462* (2013.01); *A61B 2017/3409* (2013.01); *A61B 2017/3441* (2013.01); *A61B 2017/3445* (2013.01); *A61B 2017/3466* (2013.01); *A61B 2090/0811* (2016.02)

(58) Field of Classification Search
CPC ..... A61B 1/00154; A61B 1/0016; A61B 1/01; A61B 1/313; A61B 1/3132; A61B 1/00163; A61B 1/00165; A61B 1/00167; A61B 1/00096; A61B 1/002; A61B 17/34; A61M 39/06; A61M 2039/06; A61M 2039/0235; A61M 2039/0273; A61M 2039/0279
USPC ........................ 600/104, 106, 114–115, 154; 604/164.09–164.11, 167.01–167.06
See application file for complete search history.

(56) References Cited

U.S. PATENT DOCUMENTS

| | | | |
|---|---|---|---|
| 4,927,827 | A | 5/1990 | Katoh et al. |
| 5,569,205 | A | 10/1996 | Hart et al. |
| 5,836,869 | A | 11/1998 | Kudo et al. |
| 5,879,287 | A | 3/1999 | Yoshihashi |
| 6,036,637 | A | 3/2000 | Kudo |
| 6,162,236 | A | 12/2000 | Osada |
| 8,550,984 | B2 | 10/2013 | Takemoto |
| 2003/0055437 | A1 | 3/2003 | Yasunaga |
| 2005/0096695 | A1 | 5/2005 | Olich |
| 2005/0119525 | A1* | 6/2005 | Takemoto .......... A61B 1/00154 600/114 |
| 2005/0182292 | A1* | 8/2005 | Suzuki ............... A61B 1/00133 600/104 |
| 2005/0222495 | A1 | 10/2005 | Okada et al. |
| 2005/0234297 | A1 | 10/2005 | Devierre et al. |
| 2007/0106118 | A1 | 5/2007 | Moriyama |
| 2007/0232863 | A1 | 10/2007 | Miyake et al. |
| 2007/0239171 | A1 | 10/2007 | Stefanchik et al. |
| 2007/0265502 | A1 | 11/2007 | Minosawa et al. |
| 2008/0051631 | A1 | 2/2008 | Dejima et al. |
| 2008/0281299 | A1 | 11/2008 | Menn |
| 2009/0287163 | A1* | 11/2009 | Fischvogt .......... A61B 17/3462 604/256 |
| 2010/0016659 | A1 | 1/2010 | Weitzner |
| 2010/0105983 | A1 | 4/2010 | Oneda et al. |
| 2010/0191050 | A1* | 7/2010 | Zwolinski ............... A61B 1/018 600/104 |
| 2011/0082343 | A1* | 4/2011 | Okoniewski ....... A61B 17/3423 600/208 |
| 2011/0124960 | A1 | 5/2011 | St. Onge et al. |
| 2011/0184231 | A1 | 7/2011 | Page et al. |
| 2011/0230713 | A1 | 9/2011 | Kleemann et al. |
| 2011/0257671 | A1 | 10/2011 | Trovato et al. |
| 2012/0065468 | A1* | 3/2012 | Levy .................. A61B 1/00181 600/109 |
| 2013/0012783 | A1 | 1/2013 | Vayser et al. |
| 2015/0080650 | A1 | 3/2015 | Dejima et al. |
| 2016/0022122 | A1 | 1/2016 | Dejima |
| 2016/0051280 | A1 | 2/2016 | Dejima |

FOREIGN PATENT DOCUMENTS

| | | |
|---|---|---|
| JP | 10-118076 | 5/1998 |
| JP | H10179512 | 7/1998 |
| JP | 11-342107 | 12/1999 |
| JP | 2002017752 | 1/2002 |
| JP | 2002209835 | 7/2002 |
| JP | 2002330928 | 11/2002 |
| JP | 2003088532 | 3/2003 |
| JP | 2003325436 | 11/2003 |
| JP | 2004041580 | 2/2004 |
| JP | 2004141486 | 5/2004 |
| JP | 2004180858 | 7/2004 |
| JP | 2005095634 | 4/2005 |
| JP | 2005152416 | 6/2005 |
| JP | 2005192707 | 7/2005 |
| JP | 2005287963 | 10/2005 |
| JP | 2006014960 | 1/2006 |
| JP | 2007222239 | 9/2007 |
| JP | 2007301378 | 11/2007 |
| JP | 2011528576 | 11/2011 |
| JP | 2012501695 | 1/2012 |
| WO | 2006129440 | 12/2006 |
| WO | 2011014711 | 2/2011 |
| WO | 2013176167 | 11/2013 |

OTHER PUBLICATIONS

"Office Action of Japan Counterpart Application," dated Apr. 11, 2018, with English translation thereof, p. 1-p. 5.
"Office Action of Japan Counterpart Application" with English translation thereof, dated Oct. 2, 2017, p. 1-p. 8.
Written Opinion of the International Searching Authority (Form PCT/ISA/237) of PCT/JP2014/058776, dated Jun. 24, 2014, with English translation thereof, pp. 1-12.
"Office Action of U.S. Appl. No. 14/864,887," dated Apr. 21, 2016, pp. 1-10.
"Office Action of U.S. Appl. No. 14/864,887," dated Sep. 23, 2016, pp. 1-9.
"Office Action of Japanese Related Application No. 2015-508670", with English translation thereof, dated Aug. 29, 2016, pp. 1-7.
"Office Action of U.S. Appl. No. 14/864,887," dated Dec. 28, 2016, pp. 1-6.
Written Opinion of the International Searching Authority (Form PCT/ISA/237) of PCT/JP2014/058775, dated May 20, 2014, with English translation thereof, pp. 1-10.
Written Opinion of the International Searching Authority (Form PCT/ISA/237) of PCT/JP2014/058777, dated May 20, 2014, with English translation thereof, pp. 1-11.
"Office Action of U.S. Appl. No. 14/864,904," dated Jul. 11, 2017, pp. 1-52.
"Office Action of U.S. Appl. No. 15/058,096," dated Sep. 27, 2016, pp. 1-16.
Written Opinion of the International Searching Authority (Form PCT/ISA/237) of PCT/JP2014/072994, dated Oct. 14, 2014, with English translation thereof, pp. 1-8.
"Office Action of U.S. Appl. No. 15/058,096," dated May 4, 2017, pp. 1-21.
"Office Action of Japan Related Application No. 2016-249442," dated Nov. 6, 2017, with English translation thereof, pp. 1-6.
"Office Action of U.S. Appl. No. 14/864,892," dated Apr. 4, 2017, pp. 1-22.
"Office Action of Japan Related Application No. 2015-508668," dated Aug. 29, 2016, with English translation thereof, pp. 1-8.
Written Opinion of the International Searching Authority (Form PCT/ISA/237) of PCT/JP2014/058774, dated May 13, 2014, with English translation thereof, pp. 1-13.
"Office Action of U.S. Appl. No. 14/864,892," dated Aug. 30, 2017, pp. 1-18.

* cited by examiner (A)

(B)

ENDOSCOPIC SURGERY DEVICE

CROSS-REFERENCE TO RELATED APPLICATIONS

This application is a Continuation of PCT International Application No. PCT/JP2014/058778 filed on Mar. 27, 2014, which claims priority under 35 U.S.C. § 119(a) to Japanese Patent Application No. 2013-074014 filed on Mar. 29, 2013. Each of the above application(s) is hereby expressly incorporated by reference, in its entirety, into the present application.

BACKGROUND OF THE INVENTION

Field of the Invention

The present invention relates to an endoscopic surgery device, and particularly relates to an endoscopic surgery device that can operate an endoscope and a treatment tool which are inserted in a body cavity in interlock with each other.

Description of the Related Art

Recently, endoscopic surgery using an endoscope (rigid endoscope) such as a laparoscope is widely performed because invasion to a patient is small as compared with surgery in which laparotomy and thoracotomy, and so on, are performed. For example, in laparoscopic surgery, a trocar is inserted in multiple places of patient's abdomen, an endoscope, a treatment tool or the like is inserted in a body cavity using an insertion hole formed in the trocar as a guide, and various kinds of treatments are performed using the treatment tool while observing an observation image (endoscope image) by a monitor.

In general, a surgeon's hands are busy by the operation of treatment tools in endoscopic surgery. Therefore, the operation of an endoscope is performed by an assistant who is called a scopist. However, in a case where the assistant operates the endoscope, the surgeon has to sequentially give an instruction to the assistant, and there are problems that a work to correctly turn the direction of the endoscope to a direction desired by the surgeon is difficult and the surgeon suffers stress. Moreover, since the assistance performs an operation after the surgeon gives an instruction, there is a problem of taking time to perform a surgery. In addition, the assistant has to operate the endoscope so as not to obstruct the surgeon's surgery, and there is a problem that the operation is likely to become complicated.

Meanwhile, Japanese Patent Application Laid-Open No. 2007-301378 (PTL 1) discloses a technique that inserts a treatment tool and an endoscope from opening portions formed in different positions in a body wall into body cavities respectively in endoscopic surgery and synchronously moves the endoscope according to the movement of the treatment tool. According to this technique, since the endoscope synchronously moves according to the surgeon's operation of the treatment tool, the assistant's operation of the endoscope becomes unnecessary, the surgeon's stress with the assistant is eliminated, the surgeon can perform a surgery as desired, and therefore it is convenient. Moreover, in the technique disclosed in PTL 1, to prevent an observation image obtained by the endoscope from slightly moving and being difficult to be seen, it is determined whether the distal end of the treatment tool is in the inner region of the observation image or it is in a peripheral region, the visual field of the endoscope is not changed in a case where the distal end of the treatment tool exists in the inner region of the observation image, and the visual field of the endoscope is changed such that the distal end of the treatment tool comes to the center of the observation image in a case where the distal end of the treatment tool exists in the outer region. By this means, it becomes possible to prevent the image from being rather difficult to be seen due to the slight movement of the observation image in interlock with the slight movement of the treatment tool.

Moreover, Japanese Patent Application Laid-Open No. 2004-180858 (PTL 2) and Japanese Patent Application Laid-Open No. 2004-141486 (PTL 3) disclose a technique in which: two insertion holes are provided in an outer tube which penetrates through a body wall and is inserted in a body cavity; and the endoscope is inserted in one insertion hole and the treatment tool is inserted in the other insertion hole. According to this technique, low invasion is achieved because it is possible to reduce the number of opening portions formed in a body wall to insert the treatment tool and the endoscope in the body cavity.

SUMMARY OF THE INVENTION

However, in the technique disclosed in PTL 1, it is effective in a case where the distal end of the treatment tool moves in a direction orthogonal to the visual field direction of the endoscope, but, if a zoom device is moved in interlock with a back-and-forth movement in the axial direction of the treatment tool, the size of an observation target changes in interlock with the slight movement of the treatment tool, and there is a problem that a depth perception is difficult to be recognized.

Moreover, in PTLs 2 and 3, there is no technical idea of synchronously moving the endoscope and the treatment tool which are inserted in the same outer tube, and there is no description that suggests a problem caused when the endoscope and the treatment tool are moved in interlock with each other.

The present invention is made in view of such circumstances, and aims to provide an endoscopic surgery device with high operability that can easily obtain an image desired by a surgeon.

To achieve the above-mentioned object, an aspect of the present invention provides an endoscopic surgery device including: an endoscope including observation means (observation unit) in a distal end of a rod-shaped insertion part; a treatment tool including an operation unit in a proximal end of a rod-shaped insertion part; and an outer tube including an endoscope insertion path in which the insertion part of the endoscope is insertable in a back-and-forth movable manner, and a treatment tool insertion path in which the insertion part of the treatment tool is insertable in a back-and-forth movable manner, wherein the insertion part of the endoscope inserted in the endoscope insertion path is configured to be movable back and forth with a predetermined allowance amount, in interlock with the back-and-forth movement of the insertion part of the treatment tool inserted in the treatment tool insertion path.

According to the aspect of the present invention, in the endoscopic surgery device including the endoscope, the treatment tool and the outer tube, at the time when the insertion part of the treatment tool is operated in the back-and-forth direction, if the operation is made over the allowance amount, the insertion part of the endoscope moves in the back-and-forth direction in interlock with the movement in the back-and-forth direction of the insertion part of the treatment tool. Therefore, the insertion part of the endoscope and the insertion part of the treatment tool, which are inserted in the outer tube, move in the back-and-forth direction in an interlocked manner (in a synchronous manner). Moreover, the insertion part of the treatment tool moves in the axial direction of the outer tube with the predetermined allowance amount with respect to the insertion part of the endoscope. By this means, when the insertion part of the treatment tool is moved in the back-and-forth direction, if the movement is within a range of the allowance amount, the endoscope does not move in the back-and-forth direction. By providing the allowance amount, since the slight movement of the treatment tool is not transmitted to the endoscope by providing, it is possible to obtain an excellent endoscopic image without shake.

Therefore, it is possible to prevent the size of the observation target from varying in a case where the insertion part of the treatment tool is slightly displaced in the back-and-forth direction (in a case where a back-and-forth operation of small amplitude is performed), appropriately keep a depth perception and provide a stable observation image. Moreover, in a case where the insertion part of the treatment tool is largely displaced in the back-and-forth direction (in a case where a back-and-forth operation of large amplitude is performed), since the range of the observation image is continuously changed in interlock with the displacement of the insertion part of the treatment tool, the size of the observation target changes according to the operation of the treatment tool, an image desired by a surgeon can be easily obtained, and the operability improves.

In an aspect of the present invention, it is preferable that a back-and-forth movement amount of the insertion part of the treatment tool with respect to the outer tube is 60 mm or more, and the allowance amount in an axial direction of the insertion part of the treatment tool with respect to the insertion part of the endoscope is 10 mm to 30 mm.

According to the aspect of the present invention, in the back-and-forth movement amount of the insertion part of the treatment tool with respect to the outer tube, since a movement amount of 60 mm or more together with the allowance amount of 10 mm to 30 mm, is within a substantial use range which is normally used by a surgeon, the surgeon can operate the treatment tool without a sense of incompatibility.

Here, it is preferable that the back-and-forth movement amount of the insertion part of the treatment tool with respect to the outer tube is 80 mm or less, and it is more preferable that it is 70 mm.

Moreover, it is more preferable that the allowance amount is from 15 mm to 25 mm, and it is further preferable that it is 20 mm.

In an aspect of the present invention, it is preferable that the endoscopic surgery device includes a coupling member which is disposed inside the outer tube and configured to couple the insertion part of the endoscope and the insertion part of the treatment tool, wherein the coupling member includes: a first movable object which includes an endoscope holding member that holds the insertion part of the endoscope and is configured to move back and forth in an integral manner with the insertion part of the endoscope; and a second movable object which includes a treatment tool holding member that holds the insertion part of the treatment tool and is configured to move back and forth in an integral manner with the insertion part of the treatment tool, and one of the first movable object and the second movable object is configured to move back and forth with the allowance amount in interlock with the back-and-forth movement of another one of the first movable object and the second movable object.

According to the aspect of the present invention, by providing the coupling member including the first movable object and the second movable object in the outer tube, it is possible to move the insertion part of the endoscope and the insertion part of the treatment tool, which are inserted in the outer tube, in the back-and-forth direction in interlocked manner. In addition, even in a case where the insertion part of the treatment tool is slightly moved in the back-and-forth direction, it is possible to obtain an excellent endoscopic image without shake.

In an aspect of the present invention, it is preferable that: the first movable object is held to the outer tube through a first friction force (F1); and the second movable object holds the insertion part of the treatment tool through a second friction force (F2) larger than the first friction force (F1), is held to the first movable object through a third friction force (F3) less than the first friction force (F1) and is slid by the allowance amount with respect to the first movable object.

According to a mode of the present invention, by setting the relationship of friction force to F2>F1>F3, the endoscope smoothly moves in the back-and-forth direction in interlock with the movement in the back-and-forth direction of the treatment tool, and the treatment tool smoothly slides by the allowance amount in the back-and-forth direction of the outer tube with respect to the endoscope.

According to the present invention, the range of an observation image obtained by an endoscope is changed with an allowance with respect to the forward/backward movement of a treatment tool. By this means, it is possible to prevent the size of the observation target from varying in a case where an insertion part of the treatment tool is slightly displaced in the axial direction (in a case where a back-and-forth operation of small amplitude is performed), appropriately keep a depth perception and provide a stable observation image. Moreover, in a case where the treatment tool is largely displaced in the axial direction (in a case where a back-and-forth operation of large amplitude is performed), since the range of the observation image obtained by the endoscope is changed in interlock with the displacement of the treatment tool, the size of the observation target changes according to the operation of the treatment tool, an image desired by a surgeon can be easily obtained, and the operability improves.

DETAILED DESCRIPTION OF THE EMBODIMENTS

In the following, preferable embodiments of the endoscopic surgery device according to the present invention are described in detail according to the accompanying drawings.

Figure 1:
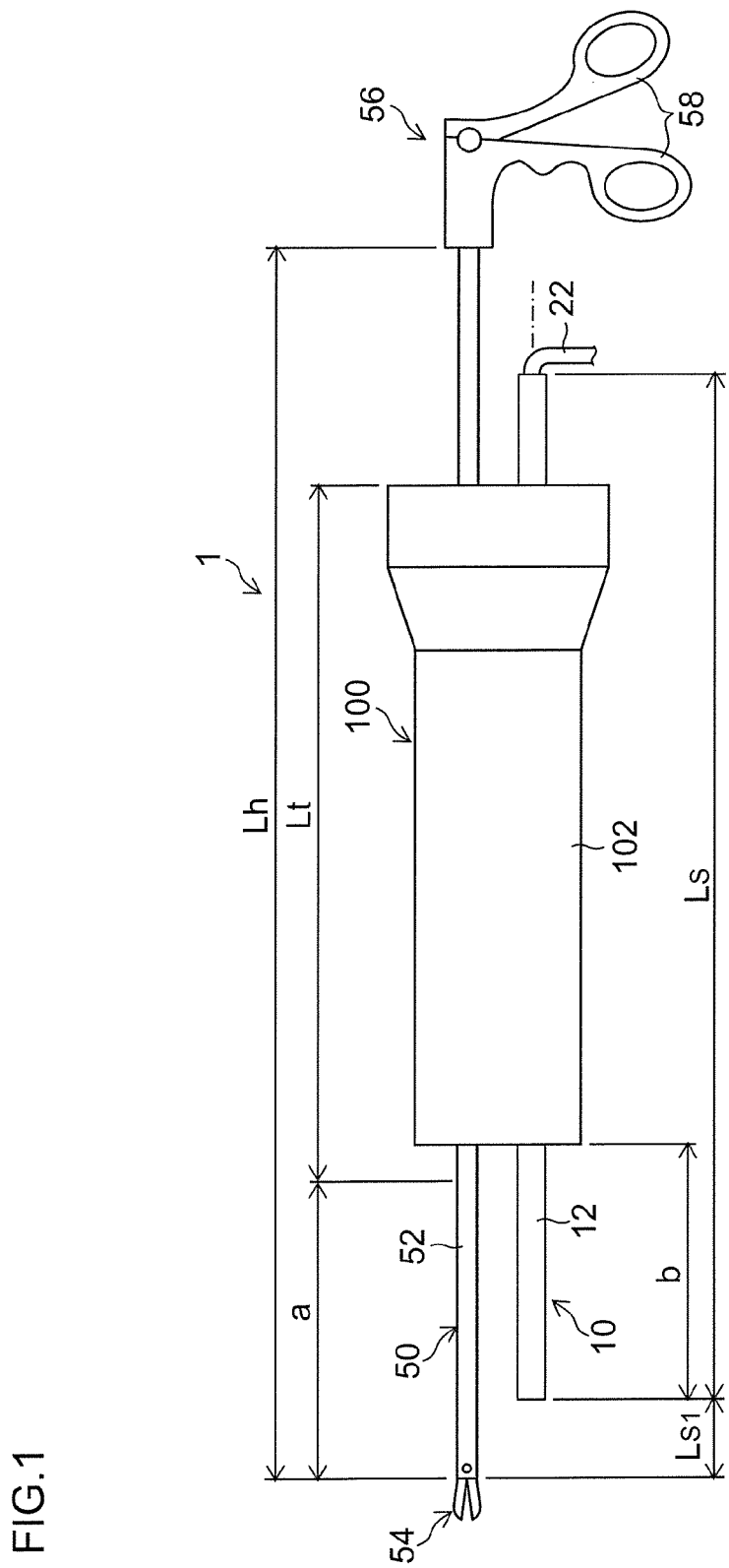
FIG. 1 is a schematic configuration diagram of an endoscopic surgery device of an embodiment.

FIG. 1 is a schematic configuration diagram of an endoscopic surgery device 1 according to the first embodiment.

First Embodiment

The endoscopic surgery device 1 includes an endoscope 10 that is inserted into a patient's body cavity and observes the inside of the body cavity, a treatment tool 50 that is inserted into the patient's body cavity and performs necessary treatment, and an outer tube 100 that guides the endoscope 10 and the treatment tool 50 into the patient's body cavity. In FIG. 1, Ls designates the length of a straight rod-shaped insertion part 12 of the endoscope 10, Lh designates the length of a straight rod-shaped insertion part 52 of the treatment tool 50, and Lt designates the length of the outer tube 100. In the endoscopic surgery device 1 of FIG. 1, the relationship among Ls, Lh and Lt is Lt<Ls<Lh, but it may have a relationship of Lt≤Ls<Lh. Moreover, "a" in FIG. 1 designates the forward/backward movement amount of the insertion part 52 of the treatment tool 50 with respect to the outer tube 100. Forward/backward movement amount "a" is set to 60 mm or more in the embodiment.

[Endoscope 10]

Figure 2:
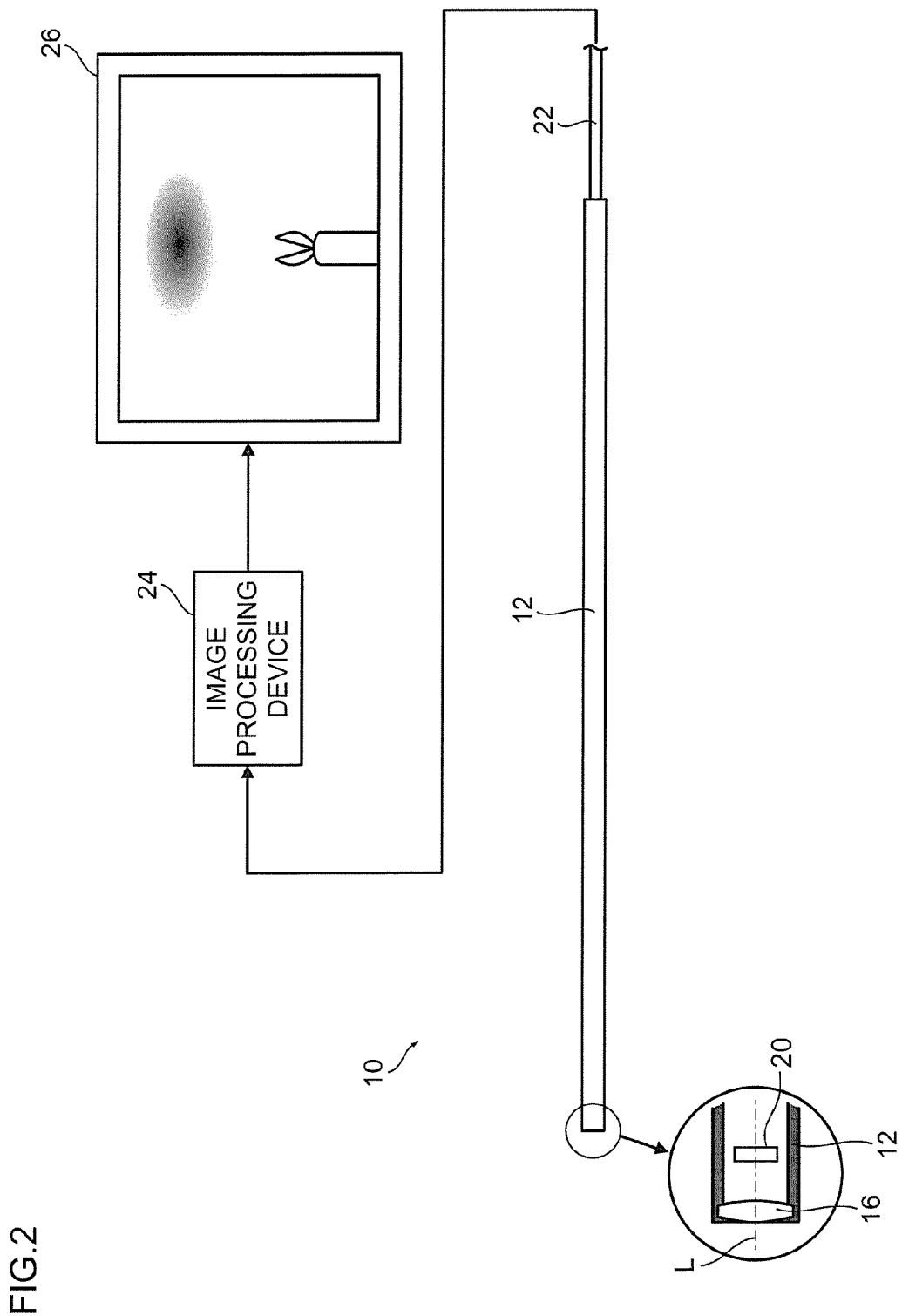
FIG. 2 is a schematic configuration diagram illustrating one example of an endoscope.

FIG. 2 is a schematic configuration diagram illustrating one example of the endoscope 10.

The endoscope 10 is a direct-view rigid endoscope such as a laparoscope. The endoscope 10 includes a straight rod-shaped insertion part 12 inserted into a patient's body cavity and a flexible cable 22 connected with a proximal end of the insertion part 12.

Observation means including an object lens 16 and an imaging element (for example, a CCD (Charge Coupled Device) and a CMOS (Complementary Metal-Oxide Semiconductor), and so on) 20 that is imaging means is built into a distal end of the insertion part 12. An observation image from the object lens 16 is formed on an image formation surface of the imaging element 20, and an image signal generated in the imaging element 20 is output to an image processing device 24 through the cable 22. The image processing device 24 performs various kinds of processing on the image signal imported from the imaging element 20 and generates a video signal that can be output to a display 26. The viewing angle of this observation means is 120 degrees, for example.

The display 26 such as a liquid crystal display is connected with the image processing device 24. The video signal generated in the image processing device 24 is output to the display 26 and displayed on the screen of the display 26 as an endoscopic image.

Here, illumination means is not provided in the endoscope 10 in FIG. 2. Illumination is performed by needle light that is another means. The external diameter of the insertion part 12 of the endoscope 10 can be made narrower by omitting the illumination means to be built in the endoscope. By this means, an external diameter of the outer tube 100 also can be made narrower, it is possible to reduce invasion to the patient's body wall.

[Needle Light 30]

Figure 3:
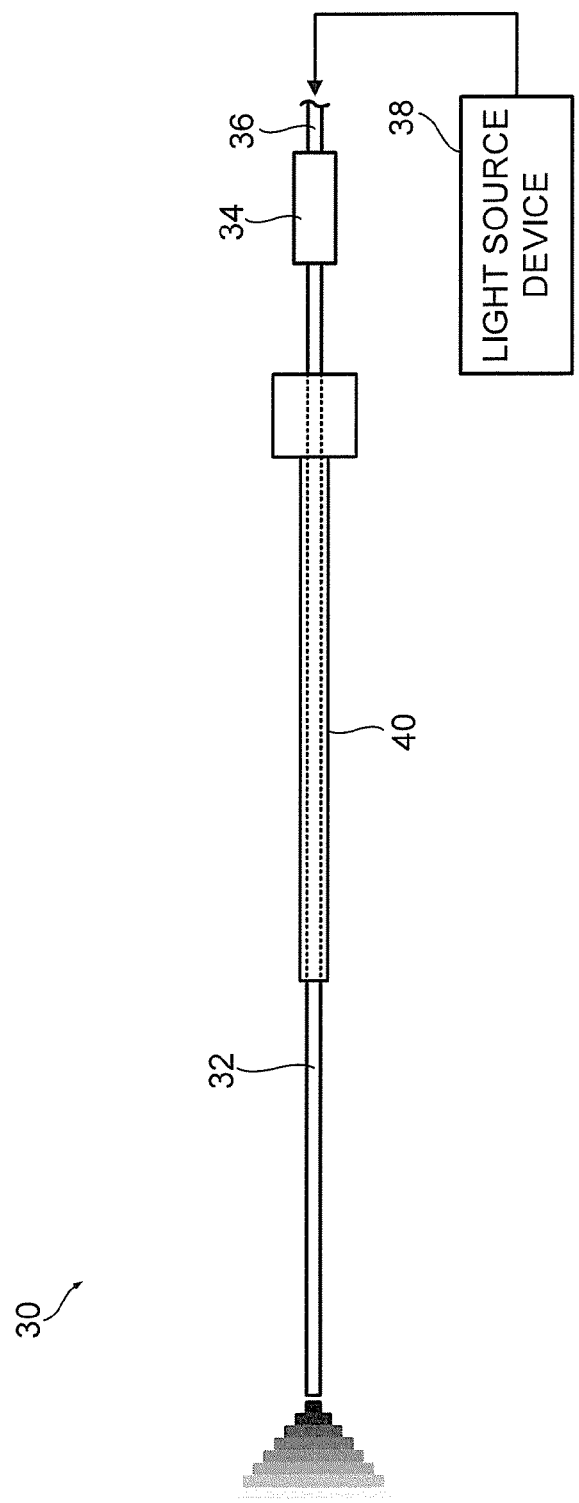
FIG. 3 is a schematic configuration diagram illustrating one example of needle light.

FIG. 3 is a schematic configuration diagram illustrating one example of the needle light 30.

The needle light 30 is a member that is inserted into the patient's body cavity and illuminates the inside of the body cavity.

The needle light 30 has a straight rod-shaped insertion part 32 thereof. An illumination window (not illustrated) is provided in a distal end of the insertion part 32, and illumination light is irradiated from this illumination window to an axial direction. An optical fiber bundle that transmits the illumination light irradiated from the illumination window is housed inside the insertion part 32.

A connection part 34 is provided in a proximal end of the needle light 30. A light source device 38 is connected with the connection part 34 through a cable 36 having flexibility. The illumination light emitted from the illumination window is supplied from the light source device 38. The needle light 30 is inserted in a body cavity through a narrow-diameter trocar 40 for needle light.

[Treatment Tool 50]

Figure 4:
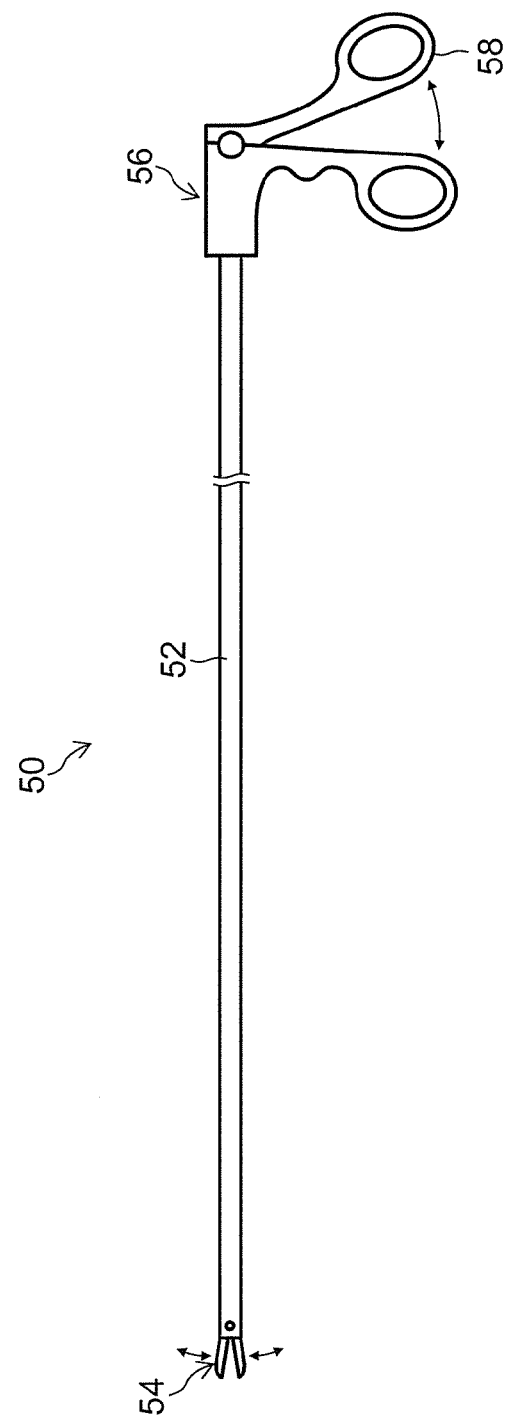
FIG. 4 is a schematic configuration diagram illustrating one example of a treatment tool.

FIG. 4 is a schematic configuration diagram illustrating one example of the treatment tool 50.

Figure 5:
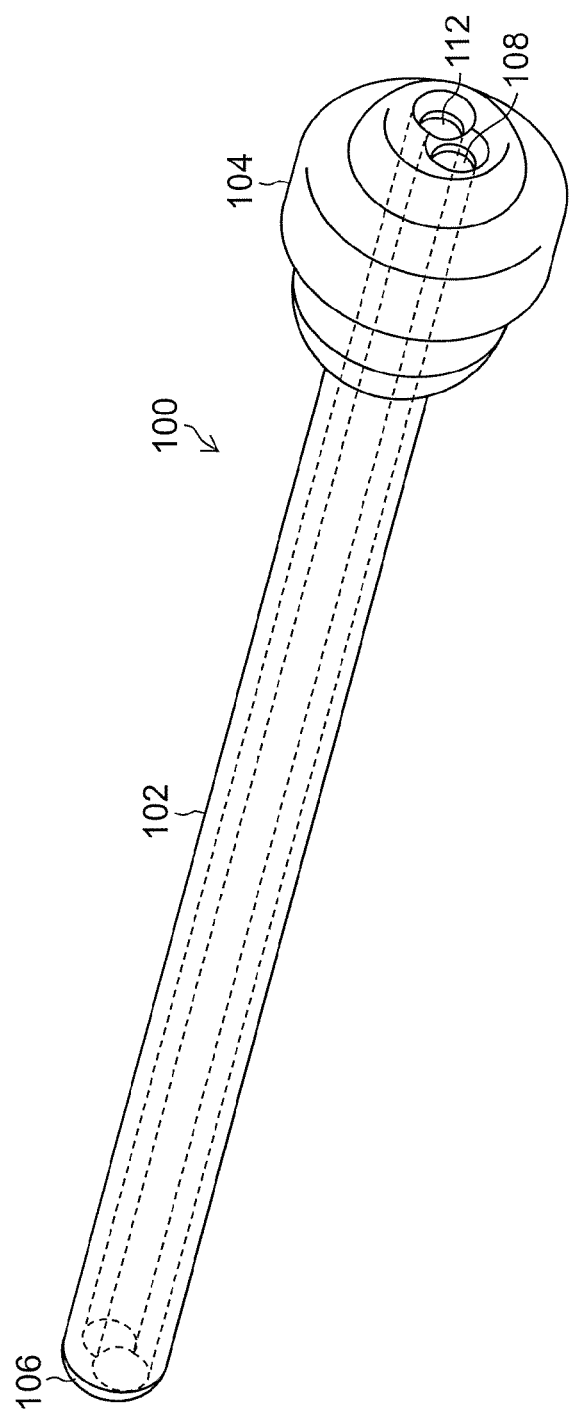
FIG. 5 is a perspective view illustrating one example of an outer tube.

The treatment tool 50 includes a straight rod-shaped insertion part 52 which is inserted in a body cavity, a treatment part 54 arranged in a distal end of the insertion part 52 and a handle 56 arranged in a proximal end of the insertion part 52. The treatment part 54 illustrated in FIG. 5 is configured to have a scissors structure, and the treatment part 54 is subjected to opening and closing operation by the opening and closing operation of the handle 56. Here, the treatment tool 50 is not limited to this, and a forceps, a laser probe, a suture instrument, a radio knife, a needle holder and an ultrasonic aspirator, and so on, can be used as a treatment tool.

[Outer Tube 100]

FIG. 5 is a perspective view illustrating one example of the outer tube 100.

The outer tube 100 is tapped into the patient's body cavity wall and guides the insertion part 12 of the endoscope 10 and the insertion part 52 of the treatment tool 50 into the patient's body cavity.

Figure 6:
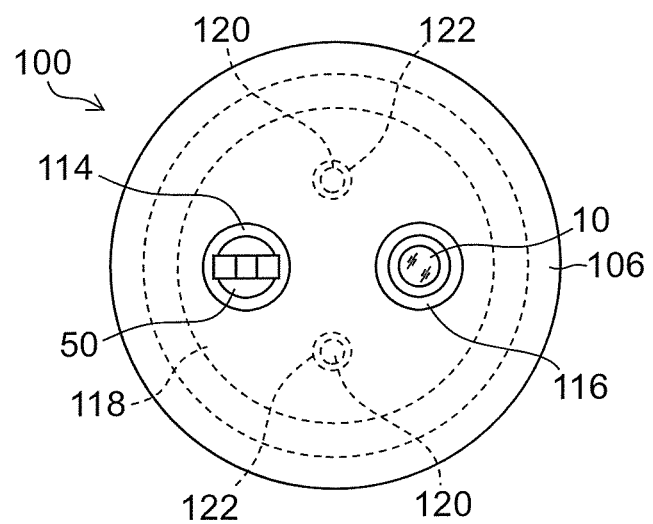
FIG. 6 is a front view of a distal end surface of an outer tube in which an endoscope and a treatment tool are inserted.
Figure 7:
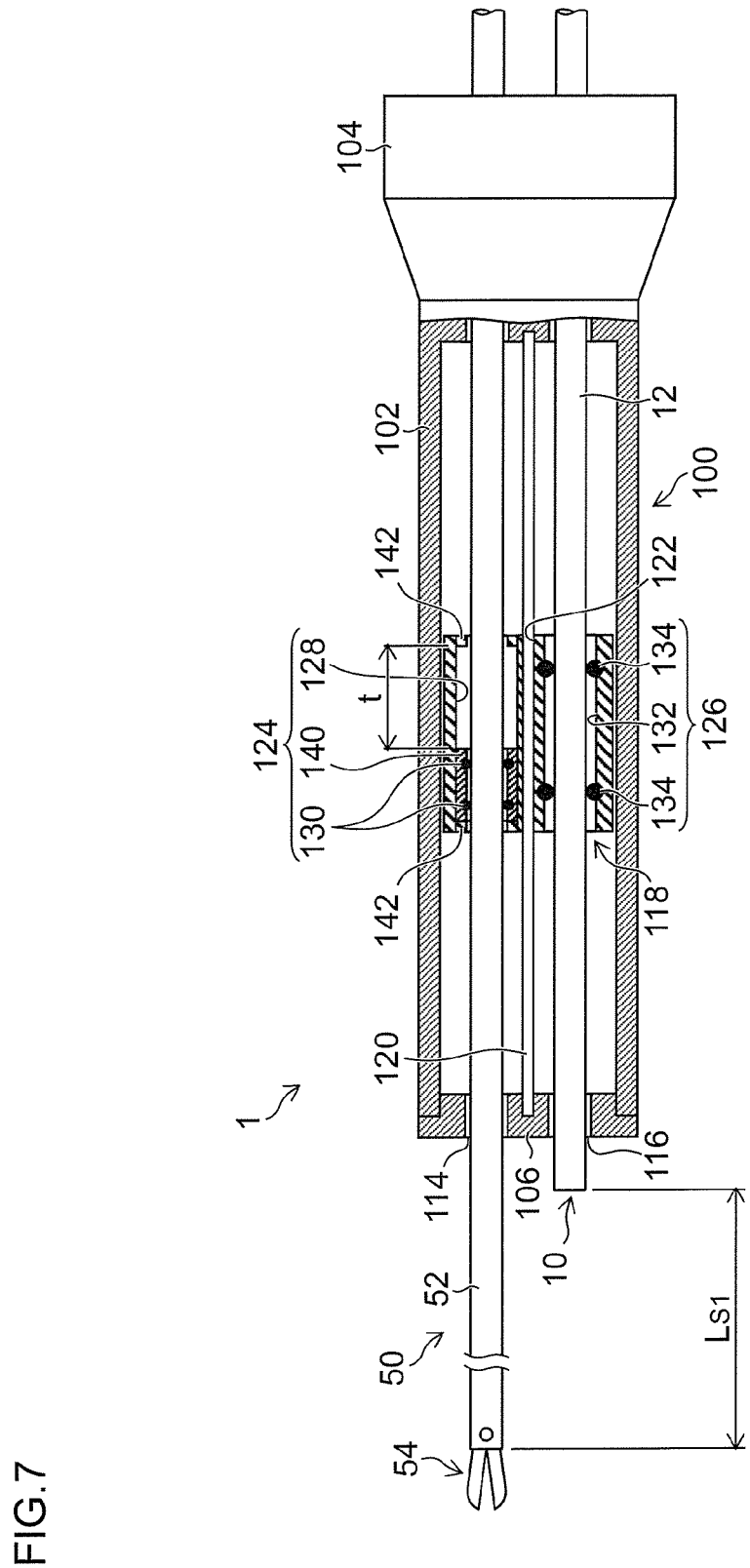
FIG. 7 is a side part cross-sectional view of an outer tube in which an endoscope and a treatment tool are inserted.
Figure 8:
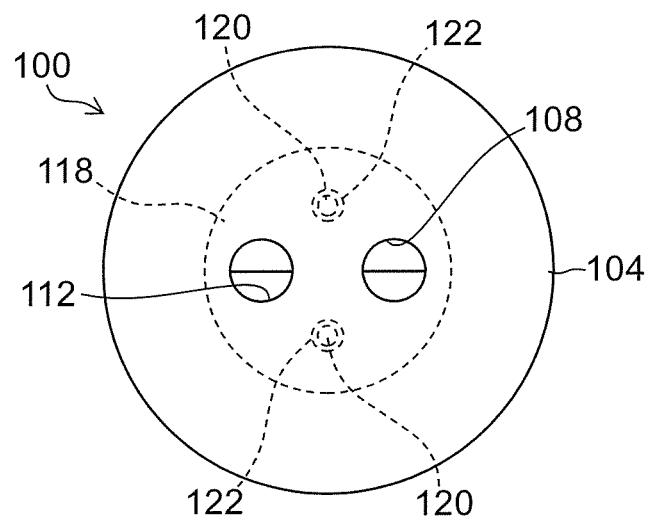
FIG. 8 is a front view of a proximal end surface of an outer tube.

FIG. 6 is a front view of the distal end surface of the outer tube 100 in which the endoscope 10 and the treatment tool 50 are inserted, FIG. 7 is a side part cross-sectional view of the outer tube 100 in which the endoscope 10 and the treatment tool 50 are inserted, and FIG. 8 is a front view of a proximal end surface of the outer tube 100.

The outer tube 100 has a cylindrical outer tube body 102. A cap 104 is attached to the proximal end of the outer tube body 102. A valve member that secures the air tightness is housed in the cap 104, and a proximal end opening portion of the outer tube body 102 is blocked by this valve member. A cap 106 is attached to a distal end of the outer tube body 102, and a distal end opening portion of the outer tube body 102 is blocked by this cap 106.

As illustrated in FIGS. 5 and 8, a treatment tool entry port 108 to insert the insertion part 52 of the treatment tool 50 in the outer tube body 102 is provided in the cap 104. The treatment tool entry port 108 is formed to have an internal diameter corresponding to an external diameter of the insertion part 52 of the treatment tool 50.

Moreover, an endoscope entry port 112 to insert the insertion part 12 of the endoscope 10 in the outer tube body 102 is provided in the cap 104. The endoscope entry port 112 is formed to have an internal diameter corresponding to an external diameter of the insertion part 12 of the endoscope 10.

As illustrated in FIG. 6, a treatment tool exit port 114 from which the insertion part 52 of the treatment tool 50 inserted in the outer tube body 102 is delivered is provided in the cap 106. The treatment tool exit port 114 is formed to have an internal diameter corresponding to an external diameter of the insertion part 52 of the treatment tool 50. The treatment tool entry port 108 in FIG. 8 and the treatment tool exit port 114 in FIG. 6 are disposed on the same axis which is parallel to the axis of the outer tube body 102. By this means, as illustrated in FIG. 7, the treatment part 54 of the treatment tool 50 inserted from the treatment tool entry port 108 (see FIG. 8) is delivered from the treatment tool exit port 114 (see FIG. 6). At this time, the insertion part 52 of the treatment tool 50 is delivered with a posture parallel to the axis of the outer tube body 102. Here, in the outer tube body 102, a conduit line that communicates the treatment tool entry port 108 and the treatment tool exit port 114 forms a treatment tool insertion path in which the insertion part 52 of the treatment tool 50 moves back and forth in the axial direction of the insertion part 52.

Moreover, the cap 106 in FIG. 6 is provided with an endoscope exit port 116 from which the insertion part 12 of the endoscope 10 inserted from the endoscope entry port 112 in FIG. 8 into the outer tube body 102 is delivered. The endoscope exit port 116 is formed to have an internal diameter corresponding to the external diameter of the insertion part 12 of the endoscope 10. The endoscope entry port 112 (see FIG. 8) and the endoscope exit port 116 (see FIG. 6) are disposed on the same axis and which is parallel to the axis of the outer tube body 102. By this means, as illustrated in FIG. 7, the distal end part of the endoscope 10 inserted from the endoscope entry port 112 (see FIG. 8) is delivered from the endoscope exit port 116 (see FIG. 6). At this time, the insertion part 12 of the endoscope 10 is delivered with a posture parallel to the axis of the outer tube body 102. Here, in the outer tube body 102, a conduit line that communicates the endoscope entry port 112 and the endoscope exit port 116 forms an endoscope insertion path in which the insertion part 12 of the endoscope 10 moves back and forth in the axial direction of the insertion part 12.

[Internal Structure of Outer Tube 100]

As illustrated in FIG. 7, a slider (first movable object) 118 that is movable in a direction parallel to the axis of the outer tube body 102 is provided inside the outer tube body 102.

The slider 118 is formed in a columnar shape, which can be housed in the outer tube body 102. The slider 118 is provided so as to be guided by a pair of guide shafts 120 and reciprocately move in the outer tube body 102 along the axis of the outer tube body 102.

Each guide shaft 120 is a round rod-shaped and is disposed inside the outer tube body 102 (see FIG. 6). Moreover, proximal ends of the guide shafts 120 are supported by the cap 104, and distal ends of the guide shafts 120 are supported by the cap 106. The guide shafts 120 are disposed in parallel to the axis of the outer tube body 102.

A pair of guide holes 122 in which the pair of guide shafts 120 can be inserted is included in the slider 118. The pair of guide holes 122 is formed in parallel to the axis of the outer tube body 102. The slider 118 is movably supported by the guide shafts 120 through the guide holes 122.

The slider 118 includes a treatment tool holding part 124 that holds the insertion part 52 of the treatment tool 50 inserted in the outer tube body 102, and an endoscope holding part 126 that holds the insertion part 12 of the endoscope 10 inserted in the outer tube body 102.

The endoscope holding part 126 includes an endoscope holding hole 132 in which the insertion part 12 of the endoscope 10 is inserted, and a pair of O-rings 134 disposed in the endoscope holding hole 132.

The endoscope holding hole 132 is formed penetrating the slider 118. The endoscope holding hole 132 is formed in parallel to the axis of the outer tube body 102 and disposed on the same axis as the endoscope entry port 112 and the endoscope exit port 116.

The pair of O-rings 134 is provided in two front and rear positions inside the endoscope holding hole 132. The internal diameter of this O-ring 134 is set to be slightly smaller than the external diameter of the insertion part 12 of the endoscope 10.

The insertion part 12 of the endoscope 10 inserted from the endoscope entry port 112 into the outer tube body 102 is delivered from the endoscope exit port 116 through the endoscope holding hole 132. The endoscope 10 passes through the O-rings 134 when passing through the endoscope holding hole 132. As mentioned above, the internal diameter of each O-ring 134 is set to be slightly smaller than the external diameter of the insertion part 12 of the endoscope 10. Therefore, when passing through the endoscope holding hole 132, the insertion part 12 of the endoscope 10 is held to the endoscope holding hole 132 by the elastic force of the O-rings 134.

Here, since the hold here denotes hold by the elastic force of the O-rings 134, the holding position of the insertion part 12 of the endoscope 10 with respect to the slider 118 can be arbitrarily adjusted.

Moreover, the endoscope 10 is held by the elastic force of the O-rings 134, but the friction force between the O-rings 134 and the insertion part 12 of the endoscope 10 is set to be larger than the friction force between the guide shafts 120 and the guide holes 122 (=the friction force between the outer tube body 102 and the slider 118: F1). By this means, the slider 118 and the insertion part 12 the endoscope 10 move with respect to the outer tube body 102 in an integral manner.

The treatment tool holding part 124 includes a treatment tool holding hole 128 in which the insertion part 52 of the treatment tool 50 is inserted, a sleeve (second movable object) 140 that moves in the axial direction along the treatment tool holding hole 128, and a pair of O-rings 130 disposed in the sleeve 140. A coupling member includes the slider 118 and the sleeve 140.

The treatment tool holding hole 128 is formed penetrating the slider 118. The treatment tool holding hole 128 is formed in parallel to the axis of the outer tube body 102 and is disposed on the same axis as the treatment tool entry port 108 and the treatment tool exit port 114.

A circular stopper ring 142 is attached to both end parts of the treatment tool holding hole 128. The sleeve 140 housed in the treatment tool holding hole 128 is prevented from coming out from the treatment tool holding hole 128 by the stopper rings 142 and 142. Moreover, as for the sleeve 140, the allowance amount t in the back-and-forth direction is set by the stopper rings 142 and 142. That is, the sleeve 140 is set so as to be slidable by the allowance amount t with respect to the slider 118 between the stopper rings 142 and 142 provided in both ends of the treatment tool holding hole 128.

The sleeve 140 is formed in a cylindrical shape, housed inside the treatment tool holding hole 128 and disposed on the same axis as the treatment tool holding hole 128. That is, the sleeve 140 is disposed on the same axis as the treatment tool entry port 108 and the treatment tool exit port 114. By this means, when the insertion part 52 of the treatment tool 50 is inserted from the treatment tool entry port 108 along the axial direction, the insertion part 52 is inserted in the inner peripheral part of the sleeve 140.

The pair of O-rings 130 is provided in two front and rear positions inside the sleeve 140. The internal diameter of this O-ring 130 is set to be slightly smaller than the external diameter of the insertion part 52 of the treatment tool 50.

The insertion part 52 inserted from the treatment tool entry port 108 into the outer tube body 102 is delivered from the treatment tool exit port 114 through the treatment tool holding hole 128. When passing through the treatment tool holding hole 128, the insertion part 52 passes through the O-rings 130 disposed in an inner peripheral part of the sleeve 140. The internal diameter of the O-rings 130 is set to be slightly smaller than an external diameter of the insertion part 52 of the treatment tool 50. Therefore, when passing through the O-rings 130, the insertion part 52 is held to the sleeve 140 by the elastic force of the O-rings 130.

Here, since the hold here denotes hold by the elastic force of the O-rings 130, the holding position of the treatment tool 50 with respect to the sleeve 140 can be arbitrarily adjusted. That is, the holding position of the insertion part 52 with respect to the slider 118 can be arbitrarily adjusted. Here, Ls1 in FIG. 7 designates the minimum projection length of the distal end of the insertion part 52 of the treatment tool 50 based on the distal end of the insertion part 12 of the endoscope 10.

In the treatment tool holding part 124, the sleeve 140 is integrated with the insertion part 52 of the treatment tool 50, and the sleeve 140 moves in interlock with the back-and-forth operation of the insertion part 52.

Here, in a case where the friction force (F3) between the sleeve 140 and the treatment tool holding hole 128 is larger than the friction force (F2) between the insertion part 52 of the treatment tool 50 and the O-rings 130, the insertion part 52 slides between the insertion part 52 and the O-rings 130, and it is not possible to move the sleeve 140 with respect to the slider 118. For such a reason, the friction force (F3) between the sleeve 140 and the treatment tool holding hole 128 is set to be smaller than the friction force (F2) between the treatment tool 50 and the O-rings 130.

On the other hand, if the friction force (F3) between the sleeve 140 and the treatment tool holding hole 128 is larger than the friction force between the guide shafts 120 and the guide holes 122 (=the friction force between the outer tube body 102 and the slider 118: F1), when the treatment tool 50 is moved, the slider 118 moves with respect to the outer tube body 102 instead of the sleeve 140. For such a reason, the friction force (F1) between the guide shafts 120 and the guide holes 122 is set to be larger than the friction force (F3) between the sleeve 140 and the treatment tool holding hole 128. Moreover, the friction force (F2) between the treatment tool 50 and the O-rings 130 is set to be larger than the friction force (F1) between the guide shafts 120 and the guide holes 122.

That is, the relationship among the friction force (F1) between the guide shafts 120 and the guide holes 122, the friction force (F2) between the treatment tool 50 and the O-rings 130 and the friction force (F3) between the sleeve 140 and the treatment tool holding hole 128 are set to be F2>F1>F3.

By this means, when the insertion part 52 of the treatment tool 50 is moved in the back-and-forth direction, if the movement is not more than an allowance amount t set by the pair of stopper rings 142 and 142, the slider 118 does not move and the endoscope 10 does not synchronously move in the back-and-forth direction.

By providing such allowance amount t, for example, in a case where the insertion part 52 is slightly displaced in the back-and-forth direction (in a case where a back-and-forth operation of small amplitude is performed), it is possible to prevent an endoscopic image displayed on the display 26 from shaking. Therefore, it is possible to provide an easily visible endoscopic image without shake.

Here, in the above-mentioned example, the insertion part (one insertion part) 12 of the endoscope 10 is held to the slider 118 and the insertion part (the other insertion part) 52 of the treatment tool 50 is held to the sleeve 140. However, even if the insertion part 12 of the endoscope 10 is held to the sleeve 140 and the insertion part 52 of the treatment tool 50 is held to the slider 118, it is possible to obtain similar operation and effect.

<<Operation of Endoscopic Surgery Device 1>>

Figure 9:
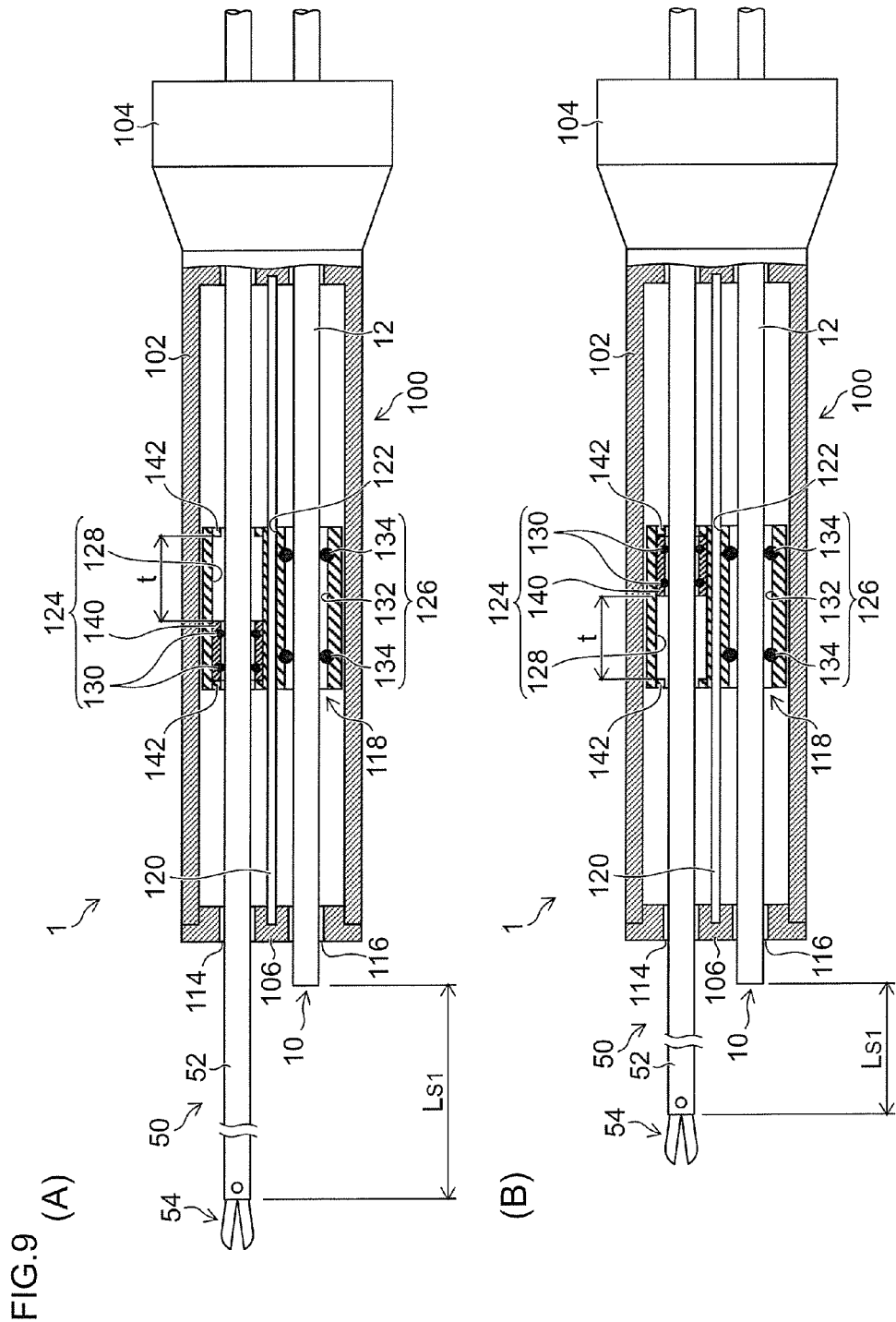
FIG. 9 is an explanatory diagram illustrating a mode when an endoscopic surgery device is used.

FIG. 9 is a diagram illustrating a mode when the endoscopic surgery device 1 is used.

The insertion part 12 of the endoscope 10 inserted in the outer tube 100 and the insertion part 52 of the treatment tool 50 are mutually held in parallel and held in parallel to the axis of the outer tube 100.

Here, the insertion part 52 of the treatment tool 50 is held to the sleeve 140, and the sleeve 140 is provided so as to be movable in the axial direction with respect to the slider 118. Further, the friction force (F3) between the sleeve 140 and the treatment tool holding hole 128 and the friction force (F1) between the guide shafts 120 and the guide holes 122 are set to be F3<F1.

As a result of this, when the insertion part 52 of the treatment tool 50 is moved in the back-and-forth direction, the endoscope 10 does not move in the back-and-forth direction and only the treatment tool 50 moves in the back-and-forth direction in the range of the allowance amount t of the sleeve 140 defined by the pair of stopper rings 142 and 142.

On the other hand, when the insertion part 52 of the treatment tool 50 moves in the back-and-forth direction (axial direction) over the range of the allowance amount t, since F2>F1 is set, the slider 118 is pushed by the sleeve 140 and moves in the back-and-forth direction in an integral manner with the treatment tool 50. As a result of this, the insertion part 12 of the endoscope 10 moves in the back-and-forth direction in interlock with the insertion part 52 of the treatment tool 50.

Specifically, when the insertion part 52 moves in the advancing direction (distal end direction) over the range of the allowance amount t of the sleeve 140, the distal end of the sleeve 140 abuts on the stopper ring 142 provided in the end part on the distal end side of the treatment tool holding hole 128, and the slider 118 moves in the advancing direction in an integral manner with the insertion part 52. As a result of this, the insertion part 12 of the endoscope 10 moves in the advancing direction together with the insertion part 52.

On the other hand, when the insertion part 52 moves in the retracting direction (proximal end direction) over the range of the allowance amount t of the sleeve 140, the proximal end of the sleeve 140 abuts on the stopper ring 142 provided in the end part on the proximal end side of the treatment tool holding hole 128, and the slider 118 moves in the retracting direction in an integral manner with the insertion part 52. As a result of this, the insertion part 12 moves in the retracting direction together with the insertion part 52.

Thus, according to the endoscopic surgery device 1, the endoscope 10 moves back and forth in the same direction in interlock with the treatment tool 50 only when the treatment tool 50 is moved back and forth over the range of the allowance amount t. Moreover, as for a back-and-forth movement with a small amplitude of the treatment tool 50 like slight shake in the range of the allowance amount t, since the movement is not transmitted to the endoscope 10, it is possible to provide an excellent endoscopic image without shake.

Here, Ls1 varies according to the allowance amount t as illustrated in portion (A) and portion (B) of FIG. 9. That is, Ls1 illustrated in portion (A) of FIG. 9 designates the maximum length of Ls1, and Ls1 illustrated in portion (B) of FIG. 9 designates the minimum length of Ls1.

<<Use Example of Endoscopic Surgery Device 1>>

Figure 10:
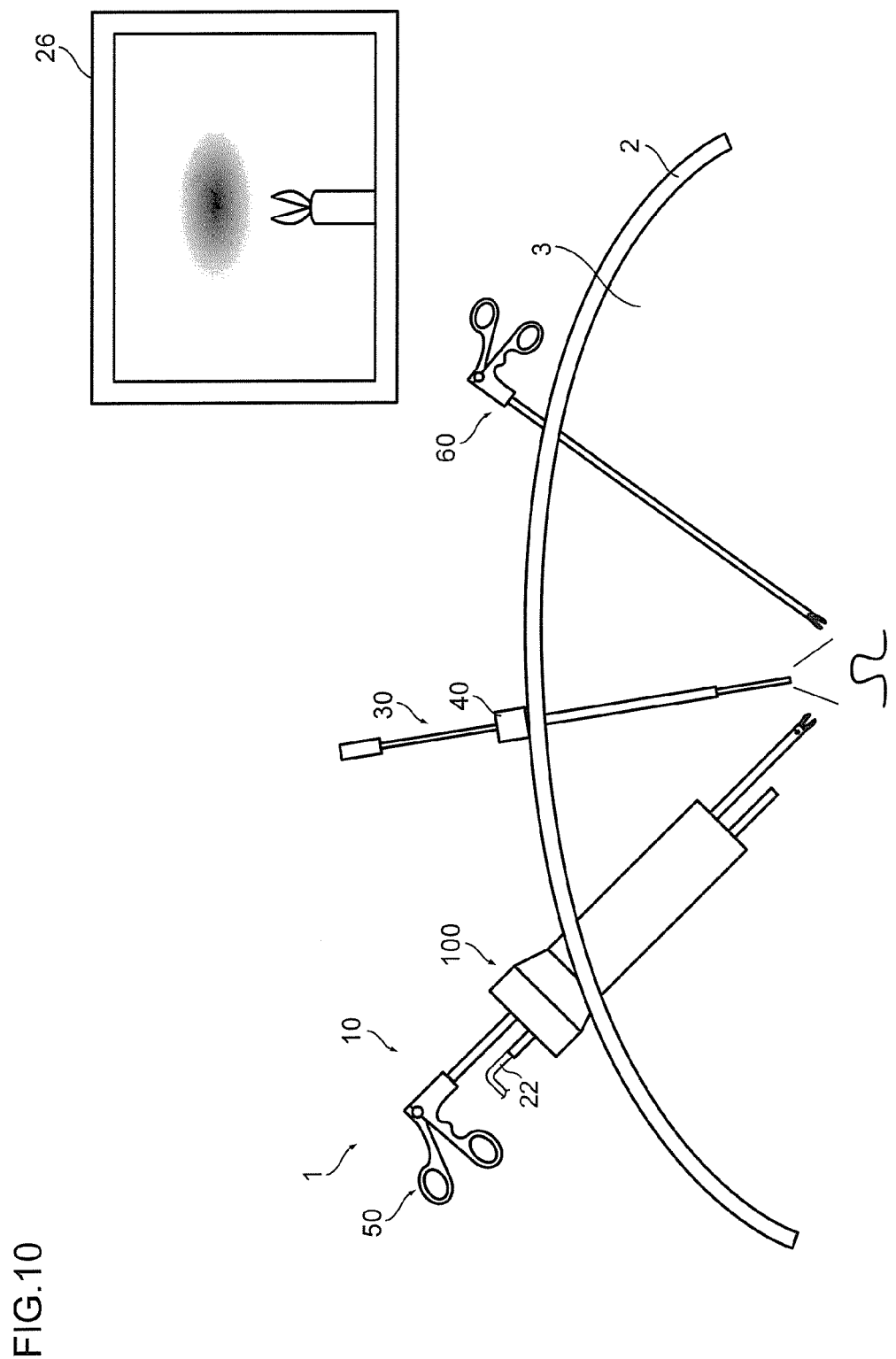
FIG. 10 is a schematic explanatory diagram illustrating one example of a surgery procedure using an endoscopic surgery device.

FIG. 10 is a schematic diagram illustrating one example of a surgery procedure using the endoscopic surgery device 1.

This example shows an example in a case where one surgeon performs treatment.

The endoscope 10 and the treatment tool 50 are inserted in a body cavity 3 through the outer tube 100 tapped into the patient's body cavity wall 2. The endoscope 10 moves back and forth in interlock with the back-and-forth movement of the treatment tool 50. By this means, an image of the treatment part is always displayed on the display 26. Moreover, it is possible to move a visual field by the movement of the treatment tool 50.

Since illumination means is not included in the endoscope 10, the needle light 30 is inserted in the body cavity 3 through the trocar 40 as illumination means. The body cavity 3 is illuminated by illumination light from the distal end of the needle light 30. Here, one needle light 30 is exemplified in this example, but multiple pieces of needle light 30 may be optionally used. As mentioned above, since the endoscope 10 is operated by the operation of the treatment tool 50, a scopist is unnecessary.

Feature of Endoscopic Surgery Device 1 of First Embodiment

It lies in coupling the insertion part 12 of the endoscope 10 and the insertion part 52 of the treatment tool 50 by a coupling member which includes the slider 118 and the sleeve 140 and which is disposed in the outer tube body 102.

As a result of this, since the insertion part 12 of the endoscope 10 moves in the back-and-forth direction in interlock with the back-and-forth direction movement of the insertion part 52 of the treatment tool 50, it is possible to synchronously move the insertion part 12 of the endoscope 10 and the insertion part 52 of the treatment tool 50, which are inserted in the outer tube 100, in the back-and-forth direction. By this means, an image of the treatment part of the treatment part 54 is always displayed on the display 26.

Moreover, it lies in coupling the insertion part 52 of the treatment tool 50 with the coupling member such that the insertion part 52 moves with respect to the insertion part 12 of the endoscope 10 with the allowance amount t in the axial direction of the outer tube 100.

By this means, it is possible to prevent the size of an observation target from varying in a case where the insertion part 52 is slightly displaced in the back-and-forth direction (in a case where the back-and-forth operation of small amplitude is performed), appropriately keep a depth perception and provide a stable observation image. Moreover, in a case where the insertion part 52 largely moves in the back-and-forth direction (in a case where a back-and-forth movement of large amplitude is performed), since the range of the observation image is continuously changed in interlock with the movement of the insertion part 52, the size of the observation target changes according to the operation of the treatment tool 50, an image desired by a surgeon can be easily obtained, and the operability improves.

Figure 11:
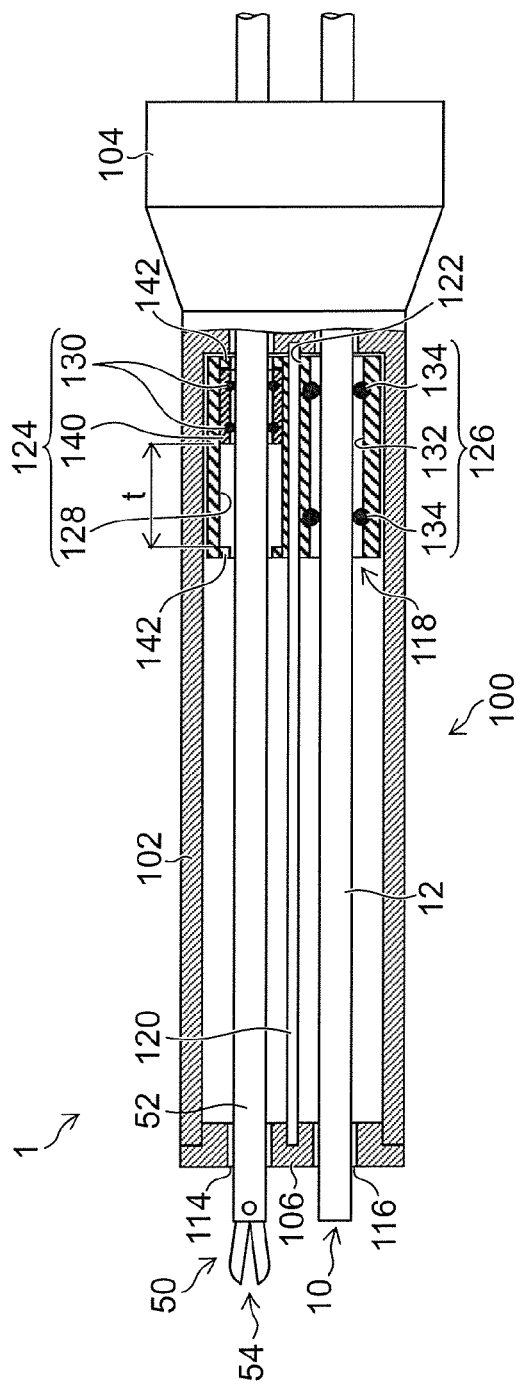
FIG. 11 is a cross-sectional view of an outer tube to describe the forward/backward movement amount of an insertion part of a treatment tool with respect to the outer tube.
Figure 13:
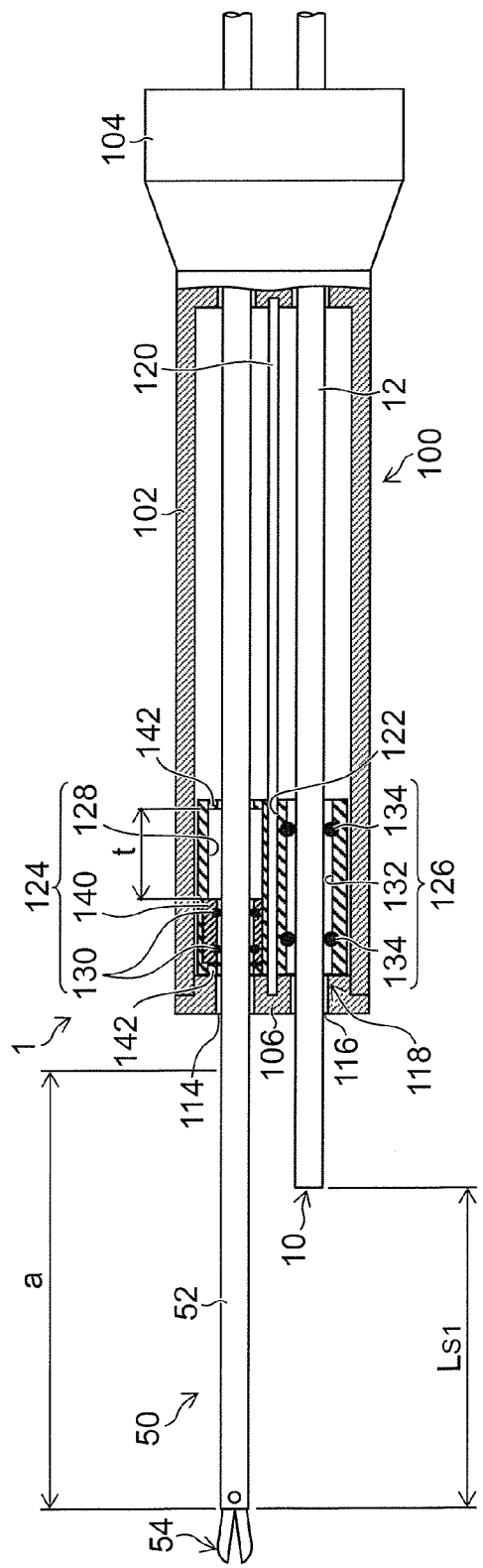
FIG. 13 is a cross-sectional view of an outer tube to describe the forward/backward movement amount of an insertion part of a treatment tool with respect to an outer tube.

In the first embodiment, the back and forth movement amount "a" of the insertion part 52 of the treatment tool 50 with respect to the outer tube 100 is set to 70 mm. That is, the back-and-forth movement amount "a" from the starting position of the back-and-forth movement of the insertion part 52 illustrated in FIG. 11 to the terminal position of the back-and-forth movement of the insertion part 52 illustrated in FIG. 13 is set to 60 mm or more. Moreover, in the first embodiment, the allowance amount t in the axial direction of the insertion part 52 of the treatment tool 50 with respect to the insertion part 12 of the endoscope 10 is set to 10 mm to 30 mm.

According to the first embodiment, in the back-and-forth movement amount "a" of the insertion part 52 of the treatment tool 50 with respect to the outer tube 100, since the movement amount of 60 mm or more, together with the allowance amount of 10 mm to 30 mm, is in a substantial use range which is normally used by the surgeon, the surgeon can operate the treatment tool without a sense of incompatibility.

Here, it is preferable that the back-and-forth movement amount "a" is 80 mm or less, and it is more preferable that it is 70 mm.

Moreover, it is preferable that the allowance amount t is 15 mm to 25 mm, and it is more preferable that it is 20 mm.

In addition, it is preferable to set the minimum projection length Ls1 to 50 mm and the allowance amount t to 20 mm Since a range of 50 mm to 70 mm, which is obtained by adding the allowance amount t=20 mm to the minimum projection length Ls1=50 mm, is in a substantial use range which is normally used by the surgeon, the surgeon can operate the treatment tool without a sense of incompatibility.

[One Example of Length of Endoscopic Surgery Device 1]

Length of outer tube 100: Lt=160 mm
Length of insertion part 12 of endoscope 10: Ls=250 mm
Length of insertion part 52 of treatment tool 50: Lh=360 mm
Viewing angle of endoscope 10: 120 degrees
Back-and-forth movement amount: a=70 mm
Allowance amount: t=20 mm
Minimum projection length: Ls1=50 mm According to this endoscopic surgery device 1, in a case where the insertion part 52 of the treatment tool 50 is moved in the back-and-forth direction within a normal use range, the treatment part 54 can be imaged in a visual field range of observation means of the endoscope 10 without individually moving the insertion part 12 of the endoscope 10 with respect to the insertion part 52 in the axial direction. Therefore, an image of the treatment site of the treatment part 54 is always displayed on the display 26 without following the treatment part 54.

[Insertion Method of Endoscope 10 and Treatment Tool 50 into Outer Tube 100]

Figure 12:
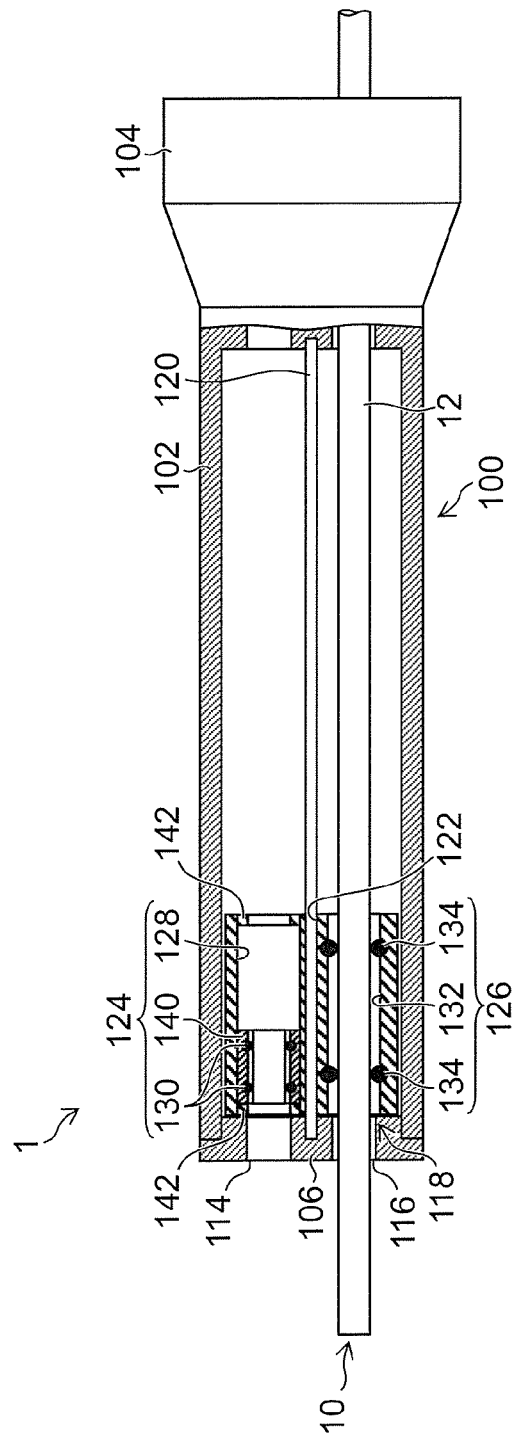
FIG. 12 is a partial cross-sectional view in which an insertion part of an endoscope is inserted in an outer tube.

FIG. 12 is a partial cross-sectional view in which the insertion part 12 of the endoscope 10 is inserted in the outer tube 100, and FIG. 13 is a partial cross-sectional view in which the insertion part 52 of the treatment tool 50 is inserted in the outer tube 100.

First, as illustrated in FIG. 12, the insertion part 12 of the endoscope 10 is inserted from the endoscope entry port 112 (see FIG. 8). The insertion part 12 inserted in the endoscope entry port 112 is delivered from the endoscope exit port 116 through the outer tube body 102. In this case, the insertion part 12 is delivered from the endoscope exit port 116 through the endoscope holding hole 132 formed in the slider 118 in an outer tube body. The O-rings 134 are provided in the endoscope holding hole 132, and the insertion part 12 passing through the endoscope holding hole 132 is held to the slider 118 by the elastic force of the O-rings 134.

Next, the insertion part 52 of the treatment tool 50 is inserted from the treatment tool entry port 108 as illustrated in FIG. 13. The insertion part 52 inserted in the treatment tool entry port 108 is delivered from the treatment tool exit port 114 through the outer tube body 102. In this case, the insertion part 52 is held to the sleeve 140 by the elastic force of the O-rings 130. At this time, it only has to set the minimum projection length Ls1 to 50 mm. Afterward, the treatment tool 50 is moved in the removal direction, and the endoscope 10 and the treatment tool 50 are located in the use positions in FIG. 7.

[Removal Method of Endoscope and Treatment Tool from Outer Tube 100]

First, the insertion part 52 of the treatment tool 50 is moved in the removal direction from the state in FIG. 7. Then, the sleeve 140 first abuts on the stopper ring 142 on the proximal end surface first, and, after this, the slider 118 moves to the proximal end side of the outer tube 100 together with the insertion part 52. Further, when the slider 118 abuts on the proximal end of the outer tube 100 and the movement of the slider 118 is restricted, the insertion part 52 is removed from the slider 118, and the insertion part 52 is removed from the outer tube 100 finally.

Next, when the insertion part 12 of the endoscope 10 is moved in the removal direction, the insertion part 12 is removed from the slider 118, and the insertion part 12 is removed from the outer tube 100 finally.

Second Embodiment

Figure 14:
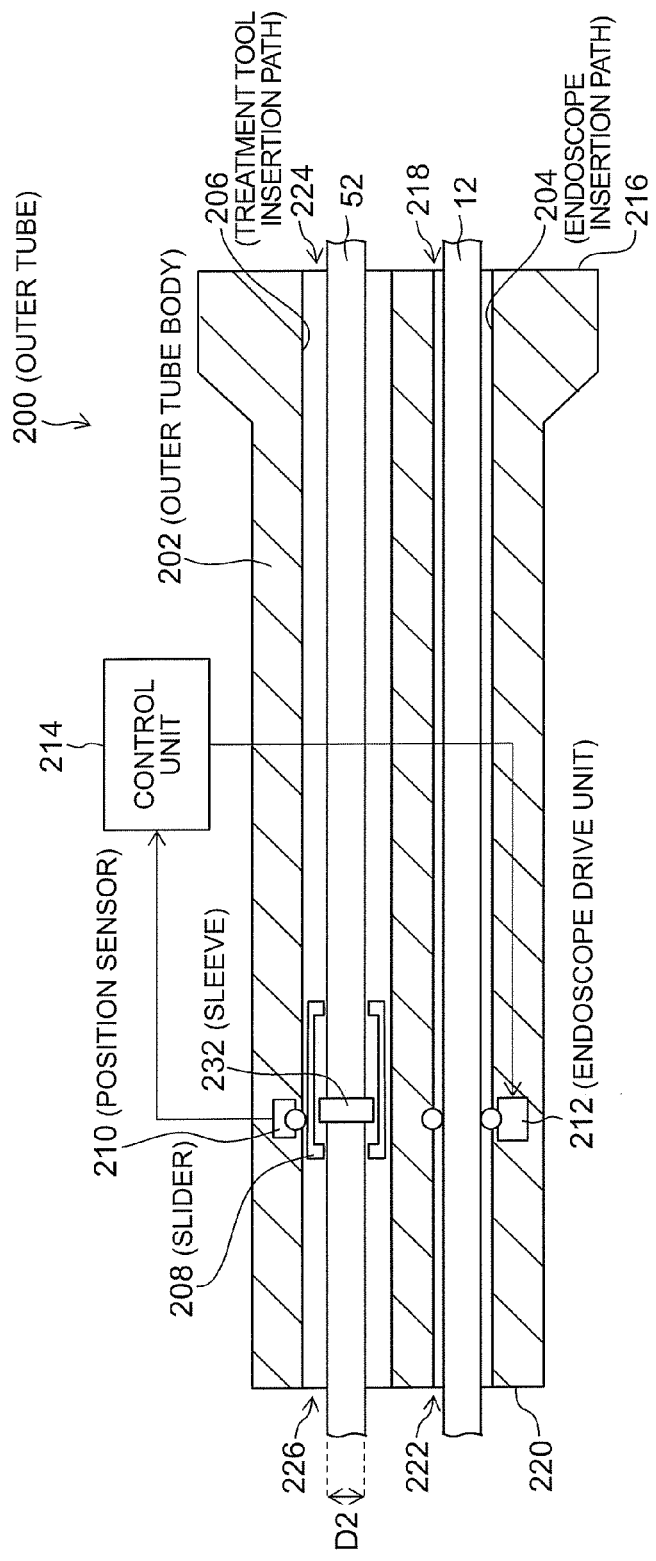
FIG. 14 is a schematic diagram illustrating an internal structure of an outer tube of an endoscopic surgery device according to the second embodiment.
Figure 15:
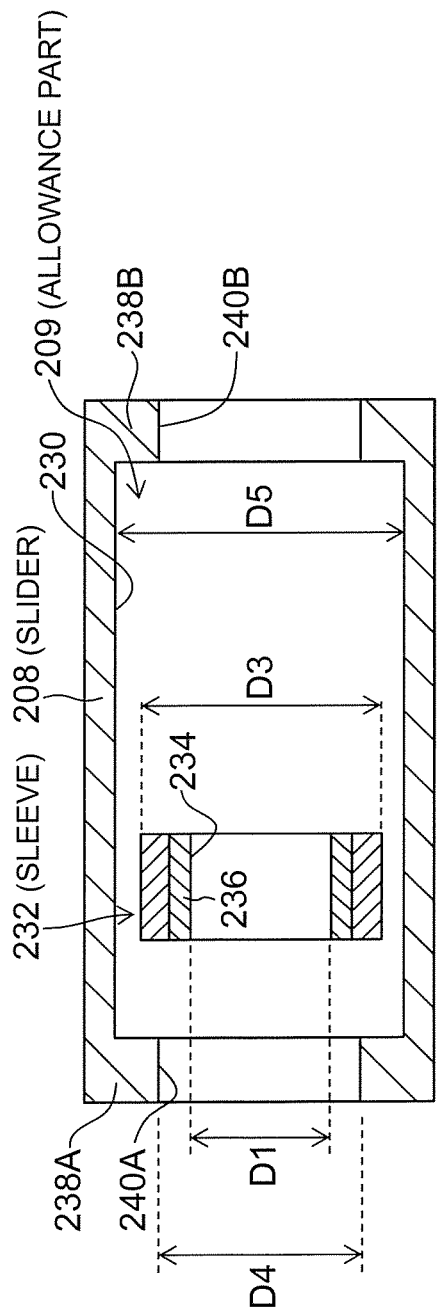
FIG. 15 is a configuration diagram illustrating structures of a slider and sleeve of the outer tube in FIG. 14.

FIG. 14 is a schematic diagram illustrating an internal structure of an outer tube 200 applied to an endoscopic surgery device according to the second embodiment. Moreover, FIG. 15 is a configuration diagram illustrating structures of a slider 208 and a sleeve 232 which are components of the outer tube 200.

As illustrated in FIG. 14, the outer tube 200 includes an outer tube body 202, an endoscope insertion path 204, a treatment tool insertion path 206, a slider 208, a position sensor 210, an endoscope drive unit 212 and a control unit 214.

The outer tube body 202 is a guide member to be penetrated into a body cavity through the patient's body wall. The endoscope insertion path 204 and the treatment tool insertion path 206 are provided inside the outer tube body 202.

The endoscope insertion path 204 is formed penetrating through the outer tube body 202 along the axial direction of the outer tube body 202 and is configured as an insertion path in which the insertion part 12 can be inserted so as to be freely movable back and forth. The endoscope insertion path 204 communicates with an endoscope entry port 218 that opens to a proximal end surface 216 of the outer tube body 202 and communicates with an endoscope exit port 222 that opens to a distal end surface 220 of the outer tube body 202. By this means, the distal end part of the insertion part 12 inserted in the endoscope entry port 218 is delivered from the endoscope exit port 222 through the endoscope insertion path 204.

The treatment tool insertion path 206 is formed penetrating through the outer tube body 202 along the axial direction of the outer tube body 202 and is configured so that the insertion part 52 can be inserted into the treatment tool insertion path 206 so as to be freely movable back and forth. The treatment tool insertion path 206 communicates with a treatment tool entry port 224 that opens to the proximal end surface 216 of the outer tube body 202 and communicates with a treatment tool exit port 226 that opens to the distal end surface 220 of the outer tube body 202. By this means, a treatment part that is the distal end part of the insertion part 52 inserted in the treatment tool entry port 224 is delivered from the treatment tool exit port 226 through the treatment tool insertion path 206.

Here, a check valve and a seal member are arranged in each of the endoscope insertion path 204 and the treatment tool insertion path 206 to secure the air tightness in a body cavity, though illustration is omitted. By this means, it is possible to prevent carbon dioxide gas introduced in the body cavity from flowing out from the body cavity through the endoscope insertion path 204 and the treatment tool insertion path 206. Moreover, a stopper portion to prevent the slider 208 described later from falling out is provided in end parts on the distal end side and proximal end side of the treatment tool insertion path 206, though illustration is omitted.

The slider 208 is an interlock member that is movable in the treatment tool insertion path 206 in interlock with the back-and-forth movement of the insertion part 52, with an allowance with respect to the movement of the insertion part 52. The slider 208 is formed in a cylindrical shape, and a guide hole 230 forming an allowance part 209 is provided in the slider 208. This guide hole 230 is formed along the axial direction, and a sleeve 232 is housed in the guide hole 230. As illustrated in FIG. 15, an external diameter D3 of the sleeve 232 is formed to be smaller than an internal diameter D5 of the guide hole 230. By this means, the sleeve 232 is configured to be movable along an axial direction of the guide hole 230.

A treatment tool holding hole 234 which is formed penetrating through the sleeve 232 along the axial direction is provided inside the sleeve 232. An inner wall part of the treatment tool holding hole 234 is formed with a cylindrical elastic member 236. An internal diameter D1 of the treatment tool holding hole 234 is formed to be slightly smaller than an external diameter (the external diameter of a part held by the treatment tool holding hole 234) D2 of the insertion part 52 (see FIG. 14). Therefore, by inserting the insertion part 52 in the treatment tool holding hole 234, the sleeve 232 is held in a state where the sleeve 232 is brought into close contact with an outer peripheral surface of the insertion part 52 by the elastic force of the elastic member 236. By this means, the sleeve 232 can move in an integral manner with the insertion part 52. Moreover, since the hold here denotes hold by the elastic force of the elastic member 236, a holding position of the insertion part 52 can be arbitrarily adjusted with respect to the sleeve 232.

Stopper portions 238A and 238B that prevent the sleeve 232 from dropping out from the guide hole 230 and restrict the movable range of the sleeve 232 are provided in both end parts in the axial direction of the slider 208. Openings 240A and 240B in which the insertion part 52 can be inserted are provided in the stopper portions 238A and 238B respectively. That is, an internal diameter D4 of each of the openings 240A and 240B is formed to be larger than the external diameter D2 of the insertion part 52 and smaller than the external diameter D3 of the sleeve 232. Therefore, when the insertion part 52 moves back and forth in a state where the sleeve 232 is held to the outer circumference part of the insertion part 52, the slider 208 does not move back and forth if the back-and-forth movement of the insertion part 52 is within an allowance range (a movable range defined by the stopper portions 238A and 238B) of the slider 208. On the other hand, in a case where the insertion part 52 moves back and forth over the allowance range of the slider 208, the sleeve 232 held to the insertion part 52 abuts on the stopper portion 238A or 238B, and the slider 208 moves back and forth in an integral manner with the insertion part 52.

The position sensor 210 illustrated in FIG. 14 detects the movement amount of the slider 208 that can move in interlock with the back-and-forth movement of the insertion part 52, with an allowance with respect to the movement of the insertion part 52. That is, the position sensor 210 is configured as detection means that has: a non-sensitive area in which a change of the relative position of the insertion part 52 with respect to the insertion part 12 is not detected even if the insertion part 52 moves back and forth, and a sensitive area in which a change of the relative position of the insertion part 52 is detected when the insertion part 12 moves back and forth, and that detects the movement amount of the insertion part 52 with respect to the outer tube body 202 in the sensitive area. As the position sensor 210, it is possible to use position sensors such as a potentiometer, an encoder and an MR (Magnetic Resistance) sensor. For example, by detecting the rotation amount of a rotation body (roller) configured to be rotatable according to the back-and-forth movement of the slider 208 using a rotary encoder and a potentiometer, and so on, it is possible to detect the movement amount of the slider 208. The detection result of the position sensor 210 is output to the control unit 214.

Here, it is assumed that the movement amount of the slider 208, which is detected by the position sensor 210, has a positive/negative value according to the movement direction. Specifically, the movement amount of the slider 208 in a case where the slider 208 moves to the diseased part side (distal end side or forward side) in a body cavity is assumed to have a positive value, and the movement amount of the slider 208 in a case where it moves to the hand side (proximal end side or backward side), which is the opposite side to the diseased part side, is assumed to have a negative value.

The endoscope drive unit 212 is drive means to move the insertion part 12 inserted in the endoscope insertion path 204 back and forth, and, for example, composed of a motor, a gear and so on. The endoscope drive unit 212 moves the insertion part 12 back and forth on the basis of a control signal output from the control unit 214. In this example, the endoscope drive unit 212 is built into the outer tube body 202, but it is not limited to this, and the endoscope drive unit may be one which moves the insertion part 12 back and forth from outside of the outer tube body 202.

The control unit 214 is endoscope movement control means to control the back-and-forth movement of the insertion part 12 through the endoscope drive unit 212 on the basis of the detection result of the position sensor 210. That is, the control unit 214 controls the back-and-forth movement of the insertion part 12 according to the movement amount of the slider 208, and moves the insertion part 12 in interlock with the back-and-forth movement of the insertion part 52, with an allowance with respect to the movement of the insertion part 52. The control unit 214 may be built into the outer tube body 202 or may be connected with the outside of the outer tube body 202 through wiring.

Figure 16:
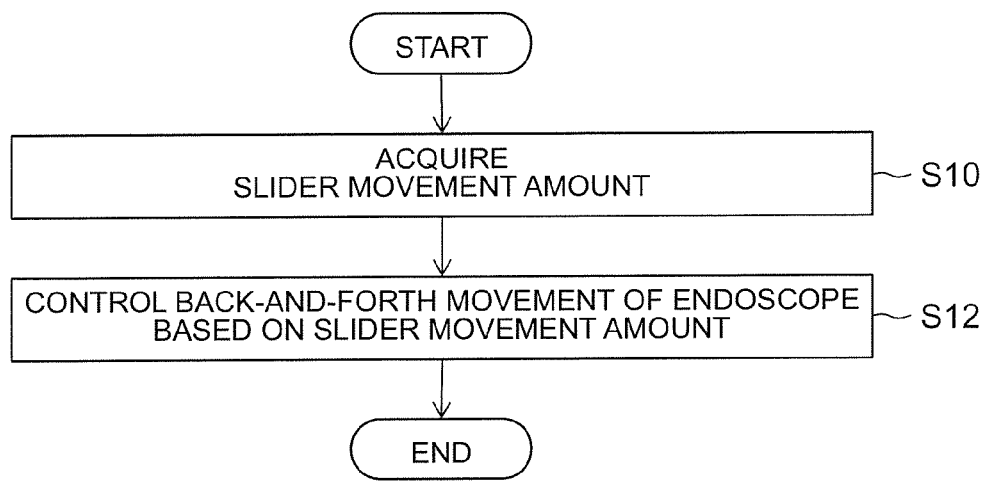
FIG. 16 is a flowchart diagram illustrating one example of processing performed by a control unit.

FIG. 16 is a flowchart diagram illustrating one example of processing performed in the control unit 214.

First, the control unit 214 acquires the movement amount of the slider 208 detected by the position sensor 210 (step S10).

Next, the control unit 214 performs control to move the insertion part 12 back and forth through the endoscope drive unit 212 on the basis of the movement amount of the slider 208 which is acquired from the position sensor 210 (step S12). Specifically, the control unit 214 outputs to the endoscope drive unit 212 a control signal for moving the insertion part 12 back and forth by the same movement amount as the movement amount of the slider 208. Then, the endoscope drive unit 212 moves the insertion part 12 back and forth on the basis of the control signal given from the control unit 214. By this means, the insertion part 12 moves back and forth by the same movement amount as the movement amount of the slider 208, that is, moves back and forth with an allowance with respect to the movement amount of the insertion part 52, in interlock with (synchronously with) the insertion part 52.

Figure 17:
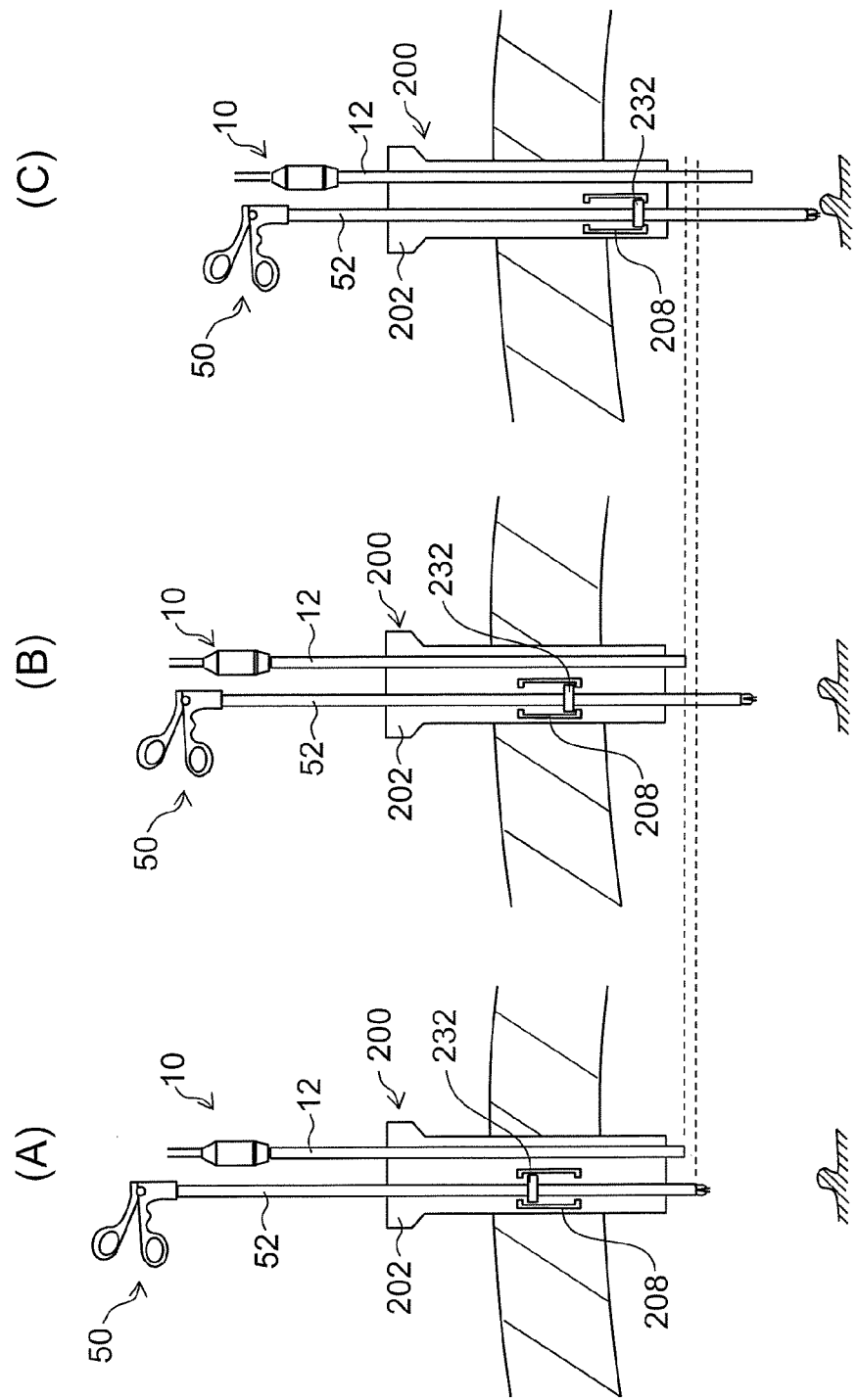
FIG. 17 is a diagram illustrating a state where an insertion part is pressed from the hand side to the patient side in a body cavity.

FIG. 17 is an explanatory diagram illustrating a state when an endoscopic surgery device according to the second embodiment is operated. FIG. 17 is a diagram illustrating a state when the insertion part 52 is pushed from the hand side into the diseased part side in a body cavity.

First, in a case where the insertion part 52 is slightly displaced in the axial direction (in a case where a back-and-forth operation of small amplitude is performed) like displacement from the state illustrated in portion (A) of FIG. 17 to the state illustrated in portion (B) of FIG. 17, only the insertion part 52 moves back and forth and the slider 208 does not move back and forth. Thus, the output of the position sensor 210 that detects the movement amount of the slider 208 becomes 0. In this case, since the insertion part 12 does not move back and forth, the range of an observation image displayed on the display 26 (see FIG. 2) does not change. Therefore, it is possible to prevent the size of the observation target from varying according to the slight displacement of the insertion part 52, appropriately keep a depth perception and obtain a stable observation image.

By contrast with this, in a case where the insertion part 52 is largely displaced in the axial direction (in a case where a back-and-forth operation of large amplitude is performed) like displacement from the state illustrated in portion (A) of FIG. 17 to the state illustrated in portion (C) of FIG. 17, the slider 208 moves back and forth in interlock with the back-and-forth movement of the insertion part 52. In this case, since the insertion part 12 moves back and forth, the range of the observation image displayed on the display 26 is continuously changed so as to follow the back-and-forth movement of the insertion part 52. By this means, since the size of the observation target changes according to the operation of the treatment tool 50, it becomes possible to easily obtain an image desired by a surgeon.

Moreover, it is also similar to a case where the insertion part 52 is drawn from the diseased part side in the body cavity to the hand side though illustration is omitted.

Here, it is preferable to perform control so as to move the insertion part 12 back and forth such that the range of the observation image displayed on the display 26 is always constant even if the insertion part 52 is moved back and forth.

As mentioned above, in the second embodiment, the insertion part 12 moves back and forth with an allowance with respect to the back-and-forth movement of the insertion part 52 by the position sensor 210.

By this means, it is possible to prevent the size of the observation target from varying in a case where the insertion part 52 is slightly displaced in the back-and-forth direction (in a case where a back-and-forth operation of small amplitude is performed), appropriately keep a depth perception and provide a stable observation image. Moreover, in a case where the insertion part 52 is largely displaced in the back-and-forth direction (in a case where a back-and-forth operation of large amplitude is performed), since the range of the observation image is continuously changed in interlock with the displacement of the insertion part 52, the size of the observation target changes according to the operation of the treatment tool 50, an image desired by a surgeon can be easily obtained and the operability is improved.

Third Embodiment

Next, the third embodiment is described. In the following, explanation is omitted for common parts with the second embodiment and characteristic parts of the third embodiment are mainly described.

Figure 18:
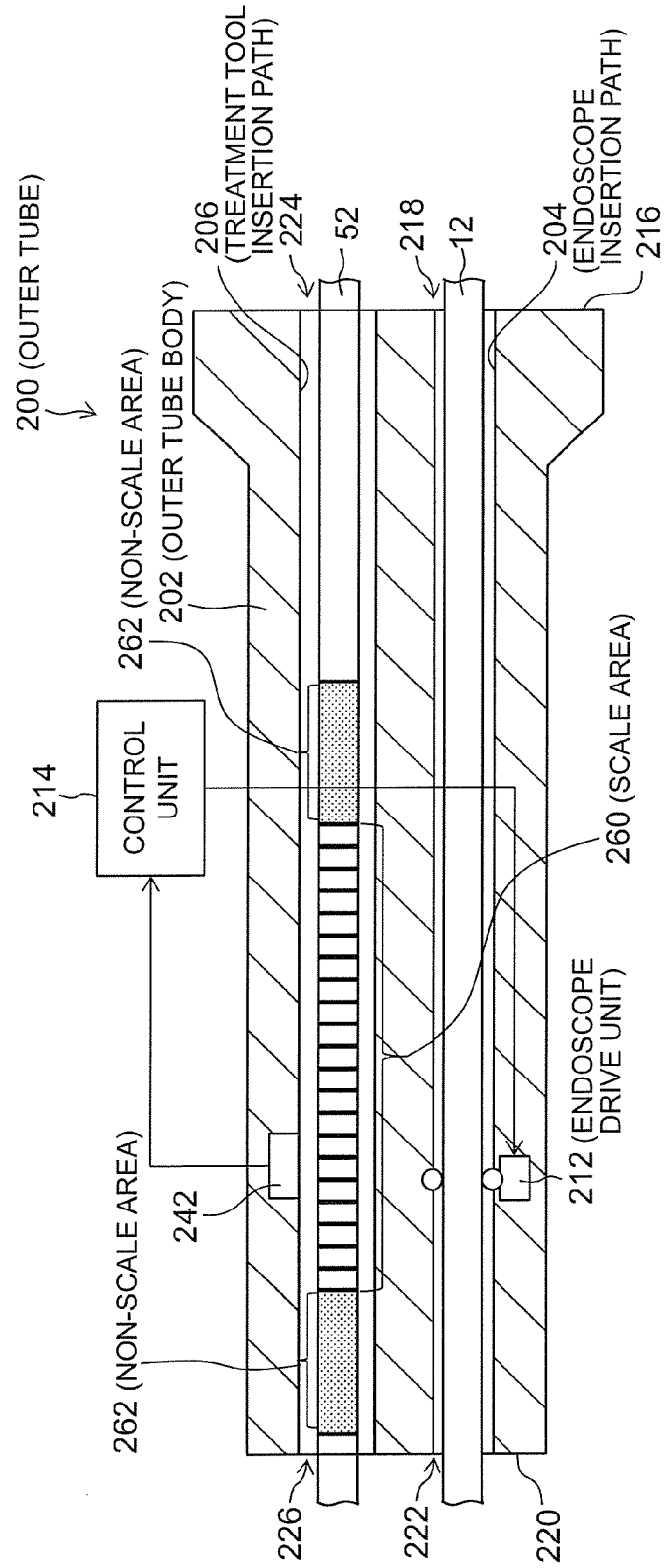
FIG. 18 is a schematic configuration diagram illustrating a main configuration of an endoscope device according to the third embodiment.

FIG. 18 is a schematic configuration diagram illustrating a main configuration of an endoscope device according to the third embodiment. In FIG. 18, the same reference numerals are assigned to components which are the same as or correspond to the components illustrated in the above-mentioned drawings.

In the third embodiment, as illustrated in FIG. 18, a scale area 260 in which a movement amount of the insertion part 52 with respect to the outer tube body 202 can be detected by a detection sensor 242 described later and a non-scale area 262 in which the above-mentioned movement amount is not detected are set in the outer peripheral surface of the insertion part 52.

The scale area 260 includes high density parts and low density parts which are alternately repeated along the axial direction of the insertion part 52.

The non-scale area 262 includes uniform density parts each having a uniform density along the axial direction of the insertion part 52, and the uniform density parts are formed on both sides of the scale area 260 (that is, on the distal end side and proximal end side of the insertion part 52 in the axial direction).

Inside the outer tube body 202, the detection sensor 242 is provided as detection means to detect a change in the relative position of the insertion part 52 with respect to the insertion part 12 when the insertion part 52 moves back and forth. This detection sensor 242 is optical reading means which optically reads the high density parts and low density parts of the scale area 260 formed in the insertion part 52, and, for example, is configured by a light emitting element and a light receiving element. For example, if the scale area 260 passes through a position facing the detection sensor 242 when the insertion part 52 moves back and forth, the movement amount of the insertion part 52 is detected by the detection sensor 242. On the other hand, in a case where the non-scale area 262 passes through the position facing the detection sensor 242, the movement amount of the insertion part 52 is not detected by the detection sensor 242. The detection result of the detection sensor 242 is output to the control unit 214.

Here, the detection sensor 242 is not limited to the optical reading means, and, for example, the detection sensor 242 may be configured by reading means which can perform magnetically reading or electrically reading. In this case, scale information corresponding to the reading means is formed in the outer peripheral surface of the insertion part 52.

The control unit 214 controls the endoscope drive unit 212 on the basis of the detection result of the detection sensor 242. That is, the control unit 214 performs control to move the insertion part 12 through the endoscope drive unit 212 according to the movement amount of the insertion part 52, which is detected by the detection sensor 242.

According to the third embodiment, the detection sensor 242 can detect the movement amount of the insertion part 52, with an allowance with respect to the back-and-forth movement of the insertion part 52. By this means, it becomes possible to move the insertion part 12 back and forth with the allowance in interlock with (synchronously with) the back-and-forth movement of the insertion part 52.

By this means, it is possible to prevent the size of an observation target from varying in a case where the insertion part 52 is slightly displaced in the back-and-forth direction (in a case where a back-and-forth operation of small amplitude is performed), appropriately keep a depth perception and provide a stable observation image. Moreover, in a case where the insertion part 52 is largely displaced in the back-and-forth direction (in a case where a back-and-forth operation of large amplitude is performed), since the range of the observation image is continuously changed in interlock with the displacement of the insertion part 52, the size of the observation target changes according to the operation of the treatment tool 50, an image desired by a surgeon can be easily obtained, and the operability improves.

Fourth Embodiment

Next, the fourth embodiment is described. In the following, explanation is omitted for common parts with the second and third embodiments, and characteristic parts of the present embodiment are mainly described.

Figure 19:
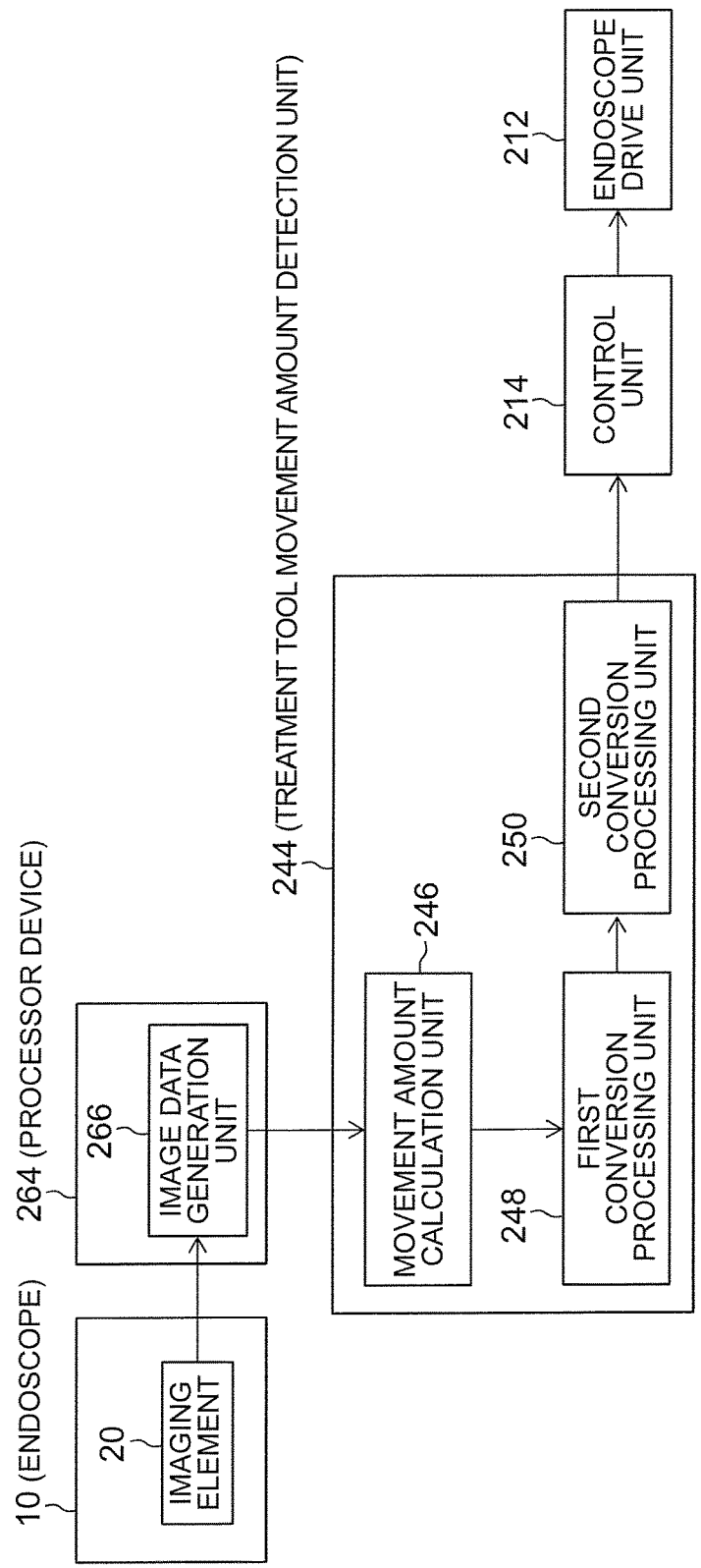
FIG. 19 is a functional block diagram illustrating a main configuration of an endoscopic surgery device according to the fourth embodiment.

FIG. 19 is a functional block diagram illustrating a main configuration of an endoscopic surgery device according to the fourth embodiment. In FIG. 19, the same reference numerals are assigned to components which are the same as or correspond to the components illustrated in the above-mentioned drawings.

In the fourth embodiment, there is provided a treatment tool movement amount detection unit 244 as detection means which detects the movement amount of the insertion part 52, with an allowance with respect to the back-and-forth movement of the insertion part 52 on the basis of image data generated by an image data generation unit 266 of the image processing device 24. Similar to the control unit 214, the treatment tool movement amount detection unit 244 may be built into the outer tube body 202 or may be connected with the outside of the outer tube body 202 through wiring.

The treatment tool movement amount detection unit 244 includes a movement amount calculation unit 246, a first conversion processing unit 248 and a second conversion processing unit 250.

Figure 20:
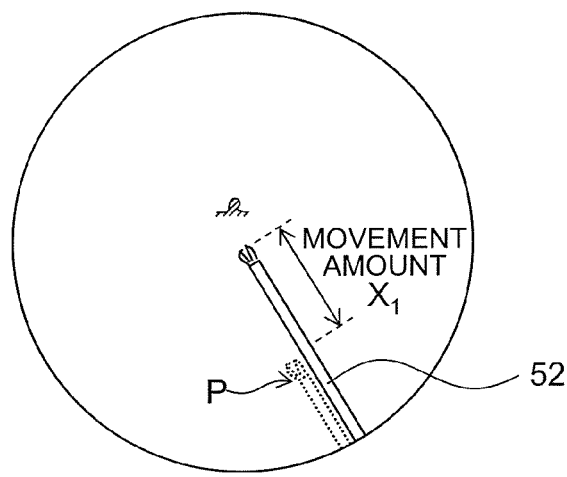
FIG. 20 is a diagram to describe the difference between a movement amount on an endoscope image and an actual movement amount.
Figure 20:
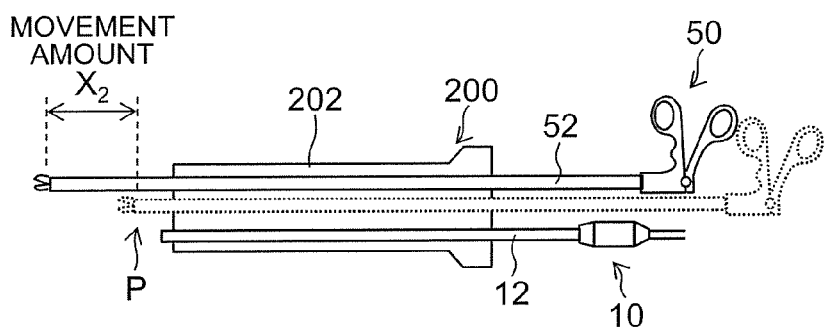

The movement amount calculation unit 246 calculates the movement amount of the insertion part 52 on the basis of the image data generated by the image data generation unit 266. The movement amount calculated at this time is a movement amount $X_1$ on an observation image as illustrated in portion (A) of FIG. 20 and is different from an actual movement amount $X_2$ illustrated in portion (B) of FIG. 20. Here, a reference character P designates the movement starting position of the insertion part 52.

The first conversion processing unit 248 converts the movement amount $X_1$ on the observation image, which is calculated by the movement amount calculation unit 246, into the actual movement amount $X_2$. Specifically, the first conversion processing unit 248 converts the movement amount $X_1$ on the observation image into the actual movement amount $X_2$ with reference to a lookup table. Here, a correspondence relationship between the movement amount $X_1$ on the observation image and the actual movement amount $X_2$ is uniquely decided from the clearance (distance) between the insertion part 52 and the insertion part 12, and the angle of view of the imaging element 20 of the endoscope 10, and so on. Data showing the correspondence relationship between these are stored in an unillustrated memory as the lookup table.

Figure 21:
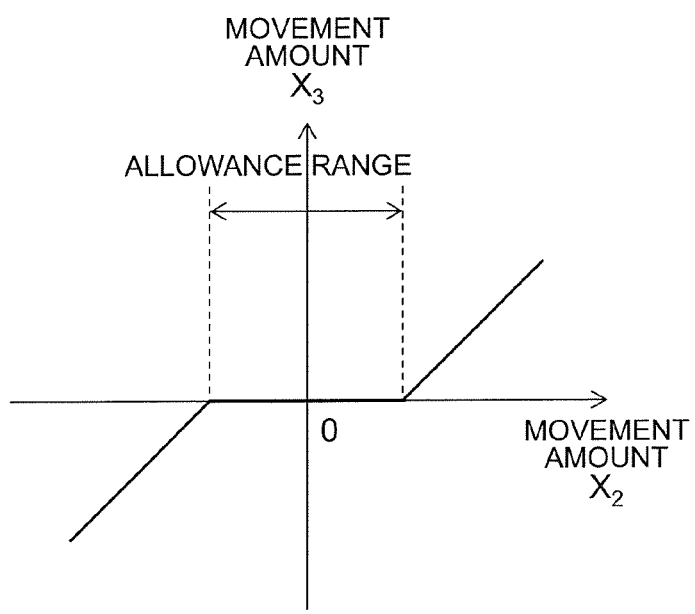
FIG. 21 is a diagram to describe conversion processing performed in a second conversion processing unit.

The second conversion processing unit 250 converts the movement amount (actual movement amount) $X_2$ of the insertion part 52, which is obtained by the first conversion processing unit 248, into a movement amount $X_3$ to which a fixed allowance amount is given. Specifically, the second conversion processing unit 250 performs conversion processing to the movement amount of the insertion part 52 according to the graph illustrated in FIG. 21. That is, the movement amount $X_3$ of the insertion part 52 is set to 0 (zero) in a case where the movement amount $X_2$ of the insertion part 52 is within an allowance range. On the other hand, the movement amount $X_3$ is set to a value obtained by subtracting a fixed value from the movement amount $X_2$ of the insertion part 52 or a value obtained by adding the fixed value to the movement amount $X_2$ of the insertion part 52 in a case where movement amount $X_2$ of the insertion part 52 is not within the above-mentioned allowance range. The movement amount $X_3$ of the insertion part 52, which is obtained in this way, is output to the control unit 214 as a detection result of the treatment tool movement amount detection unit 244.

The control unit 214 controls the back-and-forth movement of the insertion part 12 through the endoscope drive unit 212 on the basis of the detection result of the treatment tool movement amount detection unit 244.

According to the fourth embodiment, the movement amount when the insertion part 52 is moved back and forth on the basis of image data, is detected with an allowance. Therefore, it becomes possible to move the insertion part 12 back and forth with the allowance with respect to the back-and-forth movement of the insertion part 52.

By this means, it is possible to prevent the size of an observation target from varying in a case where the insertion part 52 is slightly displaced in the back-and-forth direction (in a case where a back-and-forth operation of small amplitude is performed), appropriately keep a depth perception and provide a stable observation image. Moreover, in a case where the insertion part 52 is largely displaced in the back-and-forth direction (in a case where a back-and-forth operation of large amplitude is performed), since the range of the observation image is continuously changed in interlock with the displacement of the insertion part 52, the size of the observation target changes according to the operation of the treatment tool 50, an image desired by a surgeon can be easily obtained, and the operability improves.

Fifth Embodiment

Next, the fifth embodiment is described. In the following, explanation is omitted for common parts with the second embodiment and characteristic parts of the third embodiment are mainly described.

Figure 22:
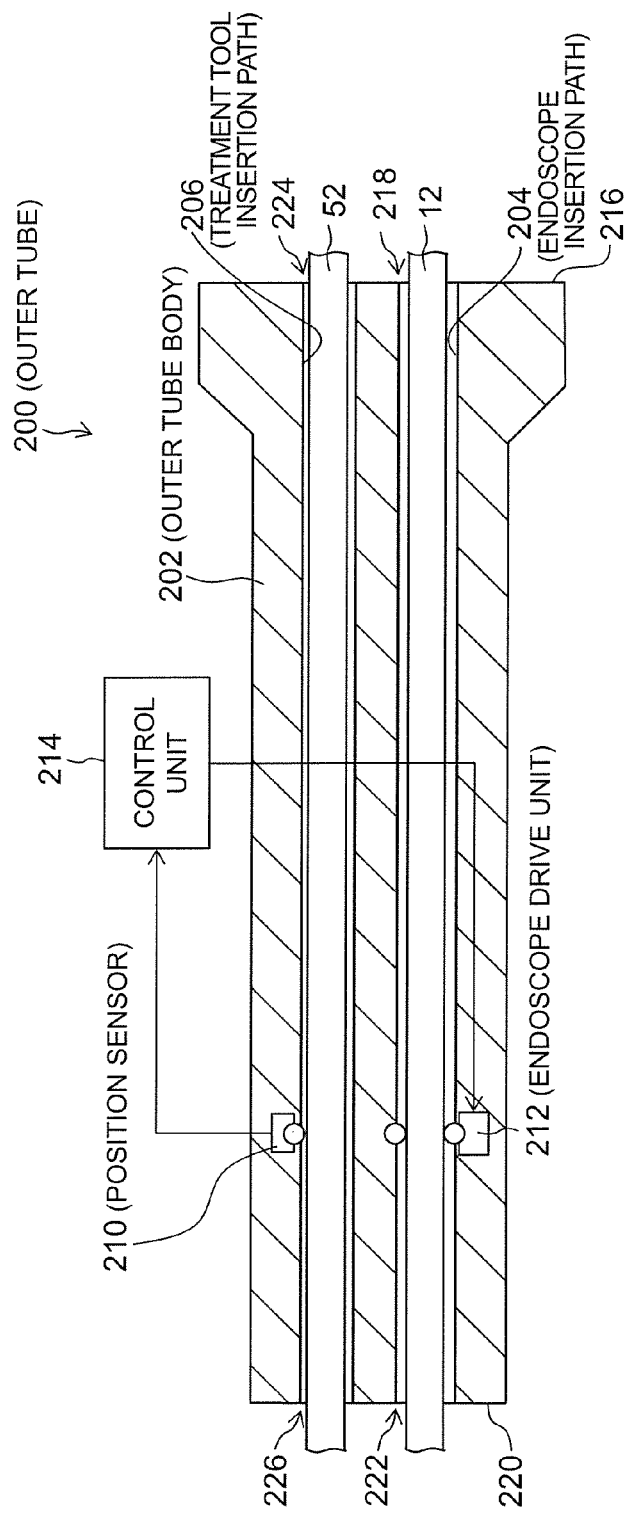
FIG. 22 is a schematic diagram illustrating an internal structure of an outer tube according to the fifth embodiment.

FIG. 22 is a schematic diagram illustrating an internal structure of the outer tube 200.

The control unit 214 of the fifth embodiment is endoscope movement control means which controls the back-and-forth movement of the insertion part 12 through the endoscope drive unit 212 on the basis of a detection result of the position sensor 210. Specifically, the control unit 214 performs control according to the graph illustrated in FIG. 23.

The position sensor 210 detects the movement amount of the insertion part 52 inserted in the treatment tool insertion path 206. That is, the position sensor 210 is formed as detection means which detects the movement amount of the insertion part 52 with respect to the outer tube body 202 when the insertion part 52 moves back and forth.

Figure 23:
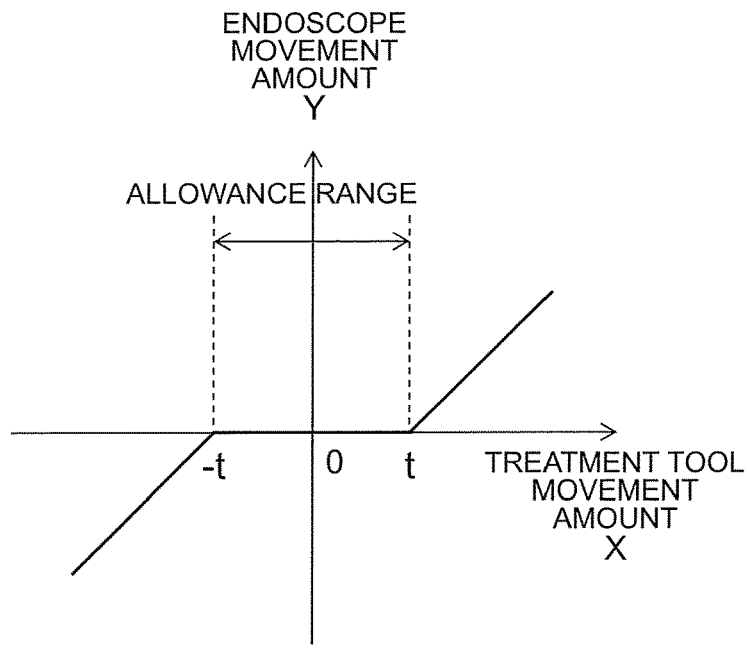
FIG. 23 is a graph illustrating the relationship between a movement amount of an insertion part and a movement amount of an insertion part.

FIG. 23 is a graph illustrating the relationship between a movement amount X of the insertion part 52 and a movement amount Y of the insertion part 12. As illustrated in FIG. 23, in a case where the movement amount X of the insertion part 52 is within a predetermined allowance range in which the movement amount X of 0 (zero) is set as a center, the control unit 214 performs control to set the movement amount Y of the insertion part 12 to 0 (zero). That is, in a case where the movement amount X of the insertion part 52 satisfies $-t \leq X \leq t$ (here, $t>0$ is assumed), the insertion part 12 is not moved back and forth.

On the other hand, in a case where the movement amount X of the insertion part 52 is not within the above-mentioned allowance range, the control unit 214 performs control to move the insertion part 12 back and forth in interlock with the back-and-forth movement of the insertion part 52. Specifically, the control unit 214 performs control to set a value obtained by adding the allowance amount t to the movement amount X of the insertion part 52 or a value obtained by subtracting the allowance amount t from the movement amount X of the insertion part 52, as the movement amount Y of the insertion part 12.

By this means, it becomes possible to move the insertion part 12 back and forth with an allowance with respect to the movement of the insertion part 52, in interlock with (synchronously with) the back-and-forth movement of the insertion part 52.

Figure 24:
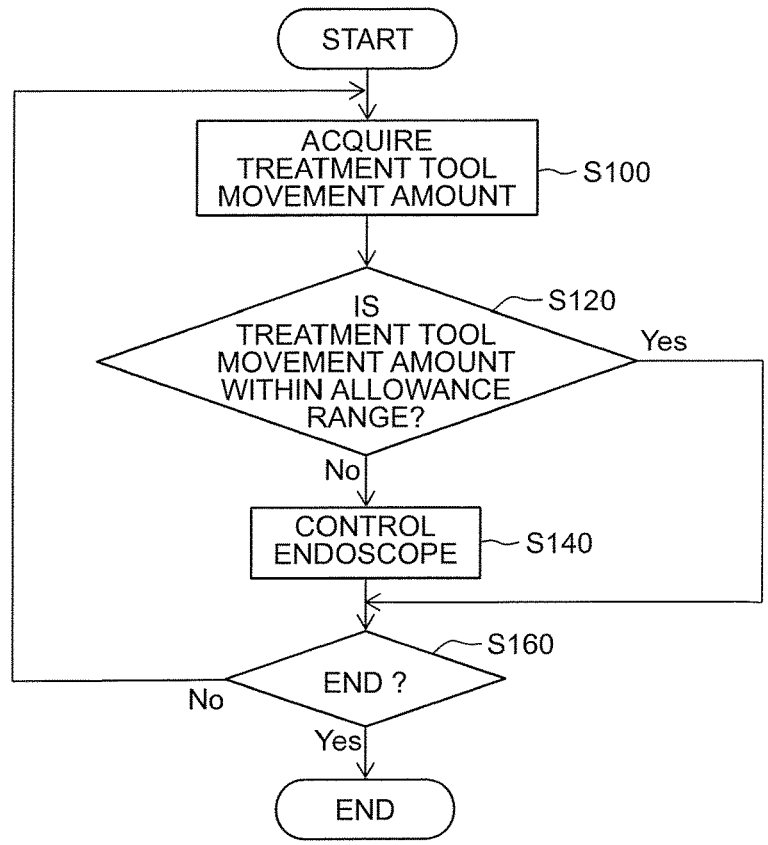
FIG. 24 is a flowchart diagram illustrating one example of processing performed in a control unit.

FIG. 24 is a flowchart diagram illustrating one example of processing performed in the control unit 214.

First, the control unit 214 acquires the movement amount of the insertion part 52 which is detected by the position sensor 210 (step S100).

Next, the control unit 214 determines whether or not the movement amount of the insertion part 52 which is acquired from the position sensor 210, is within an allowance range set beforehand (step S120). In a case where the movement amount of the insertion part 52 is within the allowance range, the control unit 214 skips step S140 and proceeds to step S160.

On the other hand, in a case where the movement amount of the insertion part 52 is not within the allowance range, as mentioned above, the control unit 214 performs control to move the insertion part 12 back and forth in interlock with the back-and-forth movement of the insertion part 52 according to the graph illustrated in FIG. 23 (step S140).

Next, the control unit 214 determines whether or not the operation has ended (step S160). In a case where it is determined that the operation does not end, the process returns to step S100 and similar processing is performed. On the other hand, in a case where it is determined that the operation has ended, control by the control unit 214 ends.

As a determination method as to whether or not the operation has ended, for example, it may be possible to install a sensor that detects whether or not the insertion part 12 or the insertion part 52 is inserted in the outer tube body 202, and determine the end of the operation according to a detection result of this sensor. Moreover, it may be possible to install an ON/OFF switch that can be manually operated, and determine the end of the operation according to the operational state of this ON/OFF switch.

By the above-mentioned configuration, since an allowance is given to the control unit 214, the insertion part 12 moves back and forth with the allowance with respect to the back-and-forth movement of the insertion part 52.

By this means, it is possible to prevent the size of an observation target from varying in a case where the insertion part 52 is slightly displaced in the back-and-forth direction (in a case where a back-and-forth operation of small amplitude is performed), appropriately keep a depth perception and provide a stable observation image. Moreover, in a case where the insertion part 52 is largely displaced in the back-and-forth direction (in a case where a back-and-forth operation of large amplitude is performed), since the range of the observation image is continuously changed in interlock with the displacement of the insertion part 52, the size of the observation target changes according to the operation of the treatment tool 50, an image desired by a surgeon can be easily obtained, and the operability improves.

Sixth Embodiment

Next, the sixth embodiment is described. In the following, explanation is omitted for common parts with the second embodiment and characteristic parts of the sixth embodiment are mainly described.

Figure 25:
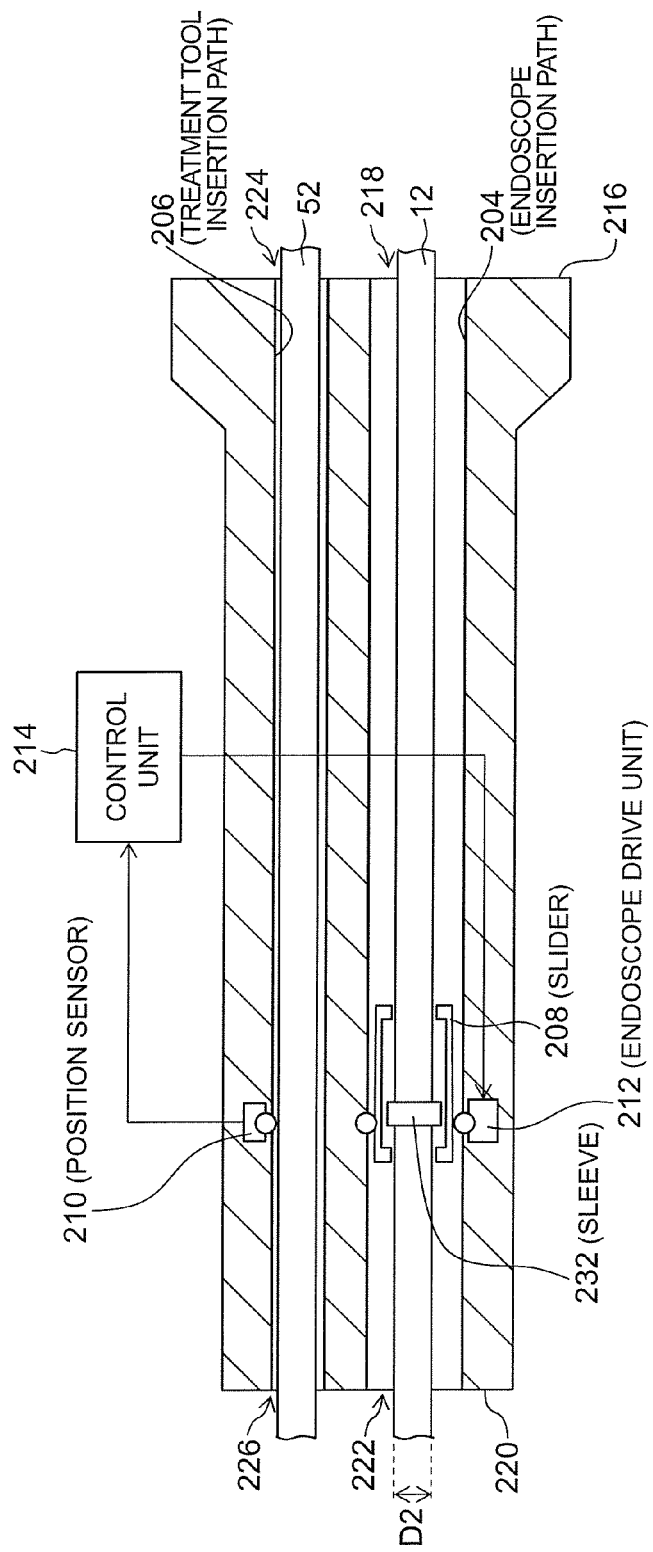
FIG. 25 is a schematic diagram illustrating an internal structure of an outer tube according to the sixth embodiment.
Figure 26:
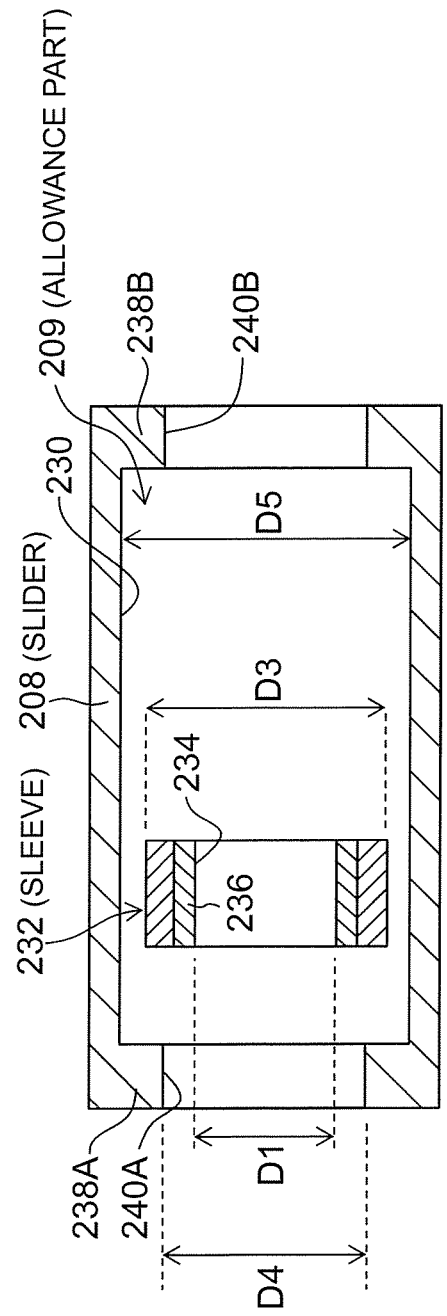
FIG. 26 is a configuration diagram illustrating structures of a slider and a sleeve.

FIG. 25 is a schematic diagram illustrating an internal structure of the outer tube 200. Moreover, FIG. 26 is a diagram illustrating structures of the slider 208 and the sleeve 232.

In the sixth embodiment, the endoscope drive unit 212 moves the insertion part 12 which is inserted in the endoscope insertion path 204 back and forth with an allowance. That is, the endoscope drive unit 212 is formed as endoscope drive means having: a non-operation area in which the insertion part 12 is not moved back and forth; and an operation area which is an area other than the non-operation area, and in the operation area the insertion part 12 is moved back and forth. For example, the endoscope drive unit 212 includes a motor, a gear, and so on, besides the slider 208 described later. The endoscope drive unit 212 moves the insertion part 12 back and forth on the basis of a control signal output from the control unit 214. In this example, the endoscope drive unit 212 is built into the outer tube body 202, but it is not limited to this, and it may move the insertion part 12 back and forth outside the outer tube body 202.

The slider 208 is a drive member that can move back and forth in the endoscope insertion path 204. By moving back and forth in the endoscope insertion path 204, this slider 208 synchronously moves the insertion part 12 back and forth with an allowance. The slider 208 is formed in a cylindrical shape, and the guide hole 230 forming an allowance part 209 is provided inside the slider 208. This guide hole 230 is formed along the axial direction, and the sleeve 232 is housed in the guide hole 230. As illustrated in FIG. 26, an external diameter D3 of the sleeve 232 is formed to be smaller than an internal diameter D5 of the guide hole 230. By this means, the sleeve 232 is formed to be movable along the axial direction of the guide hole 230.

An endoscope holding hole 234 formed penetrating along the axial direction is provided inside the sleeve 232. An inner wall part of the endoscope holding hole 234 is configured by a cylindrical elastic member 236. An internal diameter D1 of the endoscope holding hole 234 is formed to be slightly smaller than an external diameter (an external diameter of a part held by the endoscope holding hole 234) D2 of the insertion part 12 (see FIG. 25). Therefore, by inserting the insertion part 12 in the endoscope holding hole 234, the sleeve 232 is held in a state where the sleeve 232 is brought into close contact with the outer peripheral surface of the insertion part 12 by the elastic force of the elastic member 236. By this means, the sleeve 232 becomes possible to move in an integral manner with the insertion part 12.

The stopper portions 238A and 238B that prevent the sleeve 232 from dropping out from the guide hole 230 and restrict the movable range of the sleeve 232 are provided in both end parts in the axial direction of the slider 208. The openings 240A and 240B that can insert the insertion part 12 are provided in the stopper portions 238A and 238B respectively. That is, internal diameter D4 of each of the openings 240A and 240B is formed to be larger than the external diameter D2 of the insertion part 12 and smaller than the external diameter D3 of the sleeve 232. Therefore, when the slider 208 moves back and forth in a state where the sleeve 232 is held to the outer circumference part of the insertion part 12, the insertion part 12 does not move back and forth if the back-and-forth movement of the insertion part 52 is within an allowance range of the slider 208 (a movable range defined by the stopper portions 238A and 238B). On the other hand, in a case where the insertion part 52 moves back and forth over the allowance range of the slider 208, the sleeve 232 held to the insertion part 12 abuts on the stopper portion 238A or 238B and the insertion part 12 moves back and forth in an integral manner with the insertion part 12.

The control unit 214 illustrated in FIG. 25 is control means which controls the endoscope drive unit 212 on the basis of a detection result of the position sensor 210. That is, the control unit 214 controls the back-and-forth movement of the slider 208 in the endoscope drive unit 212 in proportion to the movement amount of the insertion part 52. By this control by the control unit 214, the insertion part 12 moves back and forth in proportion to the movement amount of the insertion part 52 in the operation area.

Figure 27:
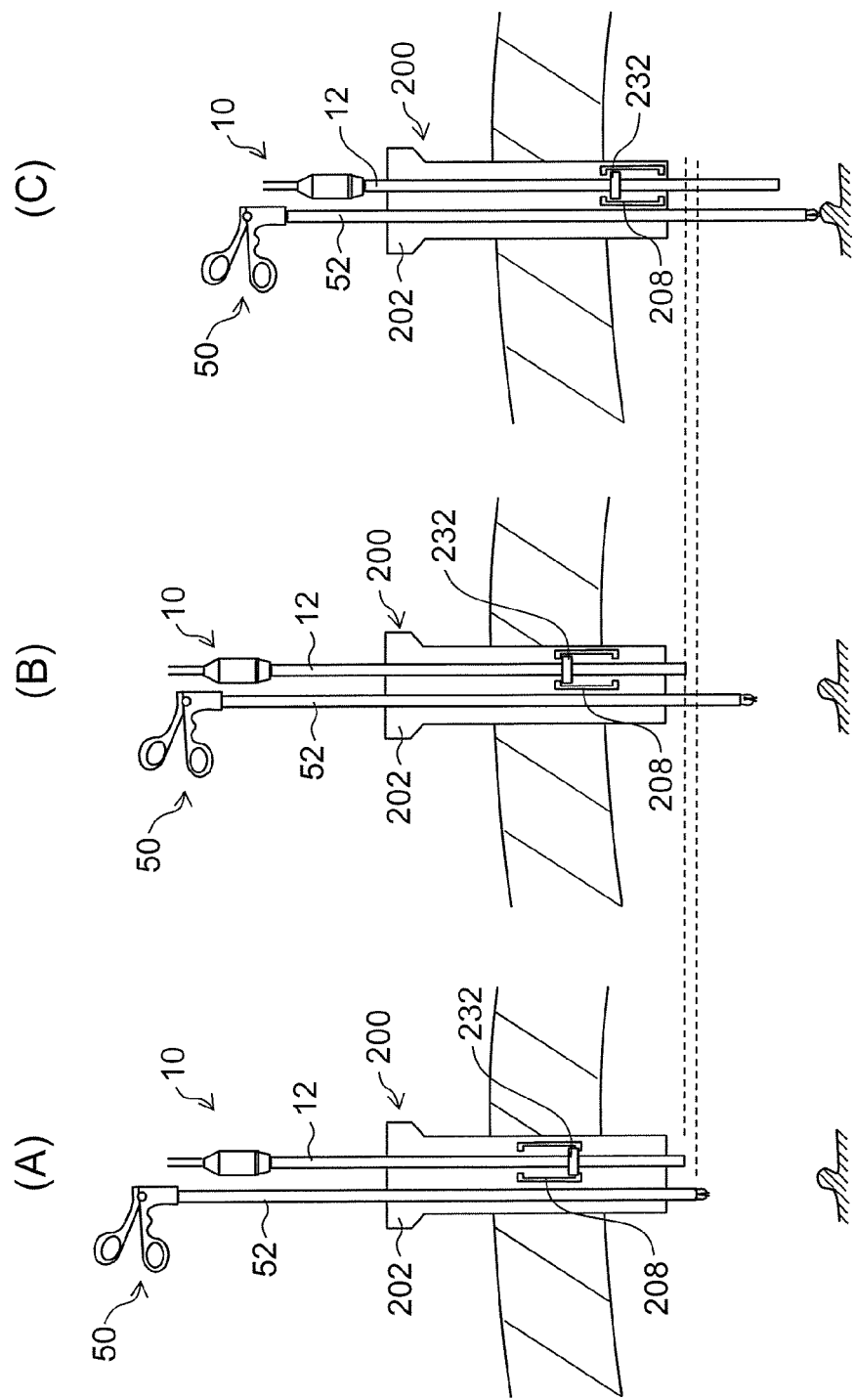
FIG. 27 is a diagram illustrating a state where an insertion part is pushed from the hand side to the patient side in a body cavity.

FIG. 27 is an explanatory diagram illustrating a state when an endoscope device according to the sixth embodiment is operated. FIG. 27 is a diagram illustrating a state when the insertion part 52 is pushed from the hand side to the diseased part side in a body cavity.

First, in a case where the insertion part 52 is slightly displaced in the axial direction (in a case where a back-and-forth operation of small amplitude is performed) like a movement from the state illustrated in portion (A) of FIG. 27 to the state illustrated in portion (B) of FIG. 27, since only the slider 208 moves back and forth, and the insertion part 12 does not move back and forth, the range of an observation image displayed on the display 26 does not change. Therefore, it is possible to prevent the size of the observation target from varying according to the slight displacement of the insertion part 52, appropriately keep a depth perception and obtain a stable observation image.

By contrast with this, in a case where the insertion part 52 is largely displaced in the axial direction (in a case where a back-and-forth operation of large amplitude is performed) like a movement from the state illustrated in portion (A) of FIG. 27 to the state illustrated in portion (C) of FIG. 27, the insertion part 12 moves back and forth in interlock with the back-and-forth movement of the slider 208. By this means, the range of the observation image displayed on the display 26 is continuously changed so as to follow the back-and-forth movement of the insertion part 52. Thus, since the size of the observation target changes according to the operation of the treatment tool 50, it becomes possible to easily obtain an image desired by a surgeon.

Moreover, it is also similar to a case where the insertion part 52 is drawn from the diseased part side in the body cavity to the hand side though illustration is omitted.

Here, it is preferable to perform control so as to move the insertion part 12 back and forth such that the range of the observation image displayed on the display 26 is always constant even if the insertion part 52 is moved back and forth.

According to the configuration above, by moving the slider 208 back and forth in the endoscope insertion path 204, the insertion part 12 moves back and forth with an allowance with respect to the back-and-forth movement of the insertion part 52.

By this means, it is possible to prevent the size of an observation target from varying in a case where the insertion part 52 is slightly displaced in the back-and-forth direction (in a case where a back-and-forth operation of small amplitude is performed), appropriately keep a depth perception and provide a stable observation image. Moreover, in a case where the insertion part 52 is largely displaced in the back-and-forth direction (in a case where back-and-forth operation of large amplitude is performed), since the range of the observation image is continuously changed in interlock with the displacement of the insertion part 52, the size of the observation target changes according to the operation of the treatment tool 50, an image desired by a surgeon can be easily obtained, and the operability improves.

What is claimed is:

1. An endoscopic surgery device, comprising:
   an endoscope;
   a treatment tool;
   an outer tube;
   a slider provided in the outer tube; and
   a sleeve provided in the outer tube;
   wherein the slider has a first stopper and a second stopper which are provided separately from each other in a longitudinal direction of the outer tube,
   wherein the sleeve is located on a first path formed between the first stopper and the second stopper, and the sleeve is only slidable between the first stopper and the second stopper relative to the slider in the longitudinal direction,
   wherein the slider has a first holding part including an endoscope holding hole that holds an insertion part of the endoscope and a second path through which the endoscope is inserted,
   wherein the sleeve has a third path through which the treatment tool is inserted and a second holding part including a treatment tool holding hole that holds an insertion part of the treatment tool inserted through the third path.

2. The endoscopic surgery device according to claim 1, wherein the treatment tool is back-and-forth movable by 60 mm or more in the longitudinal direction of the outer tube.

3. The endoscopic surgery device according to claim 1, wherein a viewing angle of the endoscope is 120 degrees.

4. The endoscopic surgery device according to claim 1, wherein a distance between the sleeve and either one of the first stopper and the second stopper is 10 mm or more and 30 mm or less.

5. The endoscopic surgery device according to claim 1, further comprising
   a first cap provided at a proximal end of the outer tube.

6. The endoscopic surgery device according to claim 5, wherein the first cap has an airtight valve.

7. The endoscopic surgery device according to claim 5, wherein the first cap has a first port through which the endoscope is inserted and a second port through which the treatment tool is inserted.

8. The endoscopic surgery device according to claim 1, further comprising
   at least one guide shaft which is provided in the outer tube along the longitudinal direction of the outer tube, one of the at least one guide shaft is located on a fourth path provided in the slider and is configured to guide the slider slidably in the longitudinal direction of the outer tube.

9. The endoscopic surgery device according to claim 8, further comprising
   a second cap which is provided at a distal end of the outer tube and to which one end of each guide shaft is fixed.

10. The endoscopic surgery device according to claim 8, wherein each guide shaft is round rod-shaped.

11. The endoscopic surgery device according to claim 8, wherein a number of guide shafts provided in the outer tube is two.

12. The endoscopic surgery device according to claim 1, wherein the first holding part has one or more O-rings.

13. The endoscopic surgery device according to claim 12, wherein at least two O-rings are disposed along the second path.

14. The endoscopic surgery device according to claim 1, wherein the second holding part has at least one O-ring.

15. The endoscopic surgery device according to claim 14, wherein at least two O-rings are disposed along the third path.

16. The endoscopic surgery device according to claim 14, wherein inner diameters of the first stopper and the second stopper are smaller than an inner diameter of the at least one O-ring.

17. The endoscopic surgery device according to claim 1, further comprising
a second cap provided at a distal end of the outer tube.

18. The endoscopic surgery device according to claim 17, wherein the second cap has a third port through which the endoscope is inserted and a fourth port through which the treatment tool is inserted.

* * * * *